(12) United States Patent
Duggan et al.

(10) Patent No.: US 7,399,764 B2
(45) Date of Patent: Jul. 15, 2008

(54) INHIBITORS OF AKT ACTIVITY

(75) Inventors: Mark E. Duggan, Harleysville, PA (US); Craig W. Lindsley, Schwenksville, PA (US); Zhijian Zhao, Wilmington (DE)

(73) Assignee: Merck & Co., Inc., Rahway, NJ (US)

( * ) Notice: Subject to any disclaimer, the term of this patent is extended or adjusted under 35 U.S.C. 154(b) by 497 days.

(21) Appl. No.: 10/530,252

(22) PCT Filed: Oct. 24, 2003

(86) PCT No.: PCT/US03/34007

§ 371 (c)(1), (2), (4) Date: Apr. 5, 2005

(87) PCT Pub. No.: WO2004/041162

PCT Pub. Date: May 21, 2004

(65) Prior Publication Data

US 2005/0288294 A1 Dec. 29, 2005

Related U.S. Application Data

(60) Provisional application No. 60/422,307, filed on Oct. 30, 2002.

(51) Int. Cl.
*A61K 31/50* (2006.01)
*A61K 31/497* (2006.01)
*C07D 241/00* (2006.01)
*C07D 487/00* (2006.01)

(52) U.S. Cl. .................. 514/249; 514/252.12; 544/236; 544/336

(58) Field of Classification Search ................. 514/249, 514/252, 12; 544/236, 336
See application file for complete search history.

(56) References Cited

U.S. PATENT DOCUMENTS

| 3,431,262 A | 3/1969 | Wendt et al. |
| 5,474,995 A | 12/1995 | Ducharme et al. |
| 6,060,491 A | 5/2000 | Pruitt et al. |
| 2002/0127214 A1 | 9/2002 | Hemmings |
| 2002/0132326 A1 | 9/2002 | Hemmings et al. |
| 2004/0102360 A1 | 5/2004 | Barnett et al. |
| 2004/0106540 A1 | 6/2004 | Barnett et al. |
| 2004/0116432 A1 | 6/2004 | Carling et al. |
| 2004/0116433 A1 | 6/2004 | Barnett et al. |
| 2004/0122012 A1 | 6/2004 | Barnett et al. |
| 2005/0130977 A1 | 6/2005 | Lindsley et al. |

FOREIGN PATENT DOCUMENTS

| GB | 9523379.7 | 11/1995 |
| GB | 9525702.8 | 12/1995 |
| GB | 9525704.4 | 12/1995 |
| JP | 54-16497 | * 2/1979 |
| WO | WO 94/10171 | 5/1994 |
| WO | WO 96/23769 | 8/1996 |
| WO | WO 96/23783 | 8/1996 |
| WO | WO 97/22360 | 6/1997 |
| WO | WO 97/49704 | 12/1997 |
| WO | WO 99/07701 | 2/1999 |
| WO | WO 99/42461 | 8/1999 |
| WO | WO 01/66525 | 9/2001 |
| WO | WO 01/91754 | 12/2001 |
| WO | WO 02/083138 | 10/2002 |
| WO | WO 03/084473 | 10/2003 |
| WO | WO 03/086279 | 10/2003 |
| WO | WO 03/086394 | 10/2003 |
| WO | WO 03/086404 | 10/2003 |

* cited by examiner

*Primary Examiner*—Golam M. Shameem
*Assistant Examiner*—Susannah Chung
(74) *Attorney, Agent, or Firm*—Matthew A. Leff; David A. Muthard

(57) ABSTRACT

The present invention is directed to compounds which contain a five-membered heterocyclic ring fused to a substituted pyrazine moiety which inhibit the activity of Akt, a serine/threonine protein kinase. The invention is further directed to chemotherapeutic compositions containing the compounds of this invention and methods for treating cancer comprising administration of the compounds of the invention.

9 Claims, No Drawings

SEQUENCE LISTING

```
<160> NUMBER OF SEQ ID NOS: 15

<210> SEQ ID NO 1
<211> LENGTH: 10
<212> TYPE: DNA
<213> ORGANISM: Artificial Sequence
<220> FEATURE:
<223> OTHER INFORMATION: Completely synthetic DNA Sequence

<400> SEQUENCE: 1
ctgcggccgc                                                          10

<210> SEQ ID NO 2
<211> LENGTH: 14
<212> TYPE: DNA
<213> ORGANISM: Artificial Sequence
<220> FEATURE:
<223> OTHER INFORMATION: Completely synthetic DNA Sequence

<400> SEQUENCE: 2
gtacgcggcc gcag                                                     14

<210> SEQ ID NO 3
<211> LENGTH: 39
<212> TYPE: DNA
<213> ORGANISM: Artificial Sequence
<220> FEATURE:
<223> OTHER INFORMATION: Completely synthetic DNA Sequence

<400> SEQUENCE: 3
cgcgaattca gatctaccat gagcgacgtg gctattgtg                          39

<210> SEQ ID NO 4
<211> LENGTH: 33
<212> TYPE: DNA
<213> ORGANISM: Artificial Sequence
<220> FEATURE:
```

<223> OTHER INFORMATION: Completely synthetic DNA Sequence

<400> SEQUENCE: 4
cgctctagag gatcctcagg ccgtgctgct ggc                                    33

<210> SEQ ID NO 5
<211> LENGTH: 24
<212> TYPE: DNA
<213> ORGANISM: Artificial Sequence
<220> FEATURE:
<223> OTHER INFORMATION: Completely synthetic DNA Sequence

<400> SEQUENCE: 5
gtacgatgct gaacgatatc ttcg                                              24

<210> SEQ ID NO 6
<211> LENGTH: 45
<212> TYPE: DNA
<213> ORGANISM: Artificial Sequence
<220> FEATURE:
<223> OTHER INFORMATION: Completely synthetic DNA Sequence

<400> SEQUENCE: 6
gaatacatgc cgatggaaag cgacggggct gaagagatgg aggtg                       45

<210> SEQ ID NO 7
<211> LENGTH: 45
<212> TYPE: DNA
<213> ORGANISM: Artificial Sequence
<220> FEATURE:
<223> OTHER INFORMATION: Completely synthetic DNA Sequence

<400> SEQUENCE: 7
cccctccatc tcttcagccc cgtcgctttc catcggcatg tattc                       45

<210> SEQ ID NO 8
<211> LENGTH: 36
<212> TYPE: DNA
<213> ORGANISM: Artificial Sequence
<220> FEATURE:
<223> OTHER INFORMATION: Completely synthetic DNA Sequence

<400> SEQUENCE: 8
gaattcagat ctaccatgag cgatgttacc attgtg                                 36

<210> SEQ ID NO 9
<211> LENGTH: 30
<212> TYPE: DNA
<213> ORGANISM: Artificial Sequence
<220> FEATURE:
<223> OTHER INFORMATION: Completely synthetic DNA Sequence

<400> SEQUENCE: 9
tctagatctt attctcgtcc acttgcagag                                        30

<210> SEQ ID NO 10
<211> LENGTH: 48
<212> TYPE: DNA
<213> ORGANISM: Artificial Sequence
<220> FEATURE:
<223> OTHER INFORMATION: Completely synthetic DNA Sequence

<400> SEQUENCE: 10
ggtaccatgg aatacatgcc gatggaaagc gatgttacca ttgtgaag                48

<210> SEQ ID NO 11
<211> LENGTH: 33
<212> TYPE: DNA
<213> ORGANISM: Artificial Sequence
<220> FEATURE:
<223> OTHER INFORMATION: Completely synthetic DNA Sequence

<400> SEQUENCE: 11
aagcttagat ctaccatgaa tgaggtgtct gtc                                33

<210> SEQ ID NO 12
<211> LENGTH: 30
<212> TYPE: DNA
<213> ORGANISM: Artificial Sequence
<220> FEATURE:
<223> OTHER INFORMATION: Completely synthetic DNA Sequence

<400> SEQUENCE: 12
gaattcggat cctcactcgc ggatgctggc                                    30

<210> SEQ ID NO 13
<211> LENGTH: 49
<212> TYPE: DNA
<213> ORGANISM: Artificial Sequence
<220> FEATURE:
<223> OTHER INFORMATION: Completely synthetic DNA Sequence

<400> SEQUENCE: 13
ggtaccatgg aatacatgcc gatggaaaat gaggtgtctg tcatcaaag               49

<210> SEQ ID NO 14
<211> LENGTH: 6
<212> TYPE: PRT
<213> ORGANISM: Artificial Sequence
<220> FEATURE:
<223> OTHER INFORMATION: Completely synthetic Amino Acid Sequence

<400> SEQUENCE: 14

Glu Tyr Met Pro Met Glu
 1               5

<210> SEQ ID NO 15
<211> LENGTH: 13
<212> TYPE: PRT
<213> ORGANISM: Artificial Sequence
<220> FEATURE:
<223> OTHER INFORMATION: Completely synthetic Amino Acid Sequence

<400> SEQUENCE: 15

Gly Gly Arg Ala Arg Thr Ser Ser Phe Ala Glu Pro Gly
 1               5                  10

INHIBITORS OF AKT ACTIVITY

PRIORITY CLAIM

This application is a §371 application of PCT/US03/34007 that was filed on Oct. 24, 2003, which claims priority from the U.S. Provisional Application No. 60/422,307, filed on Oct. 30, 2002, now expired.

BACKGROUND OF THE INVENTION

The present invention relates to compounds which contain a five-membered heterocyclic ring fused to a substituted pyrazine that are inhibitors of the activity of one or more of the isoforms of the serine/threonine kinase, Akt (also known as PKB). The present invention also relates to pharmaceutical compositions comprising such compounds and methods of using the instant compounds in the treatment of cancer.

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or BCl-$x_L$, inhibits apoptotic cell death induced by various stimuli. On the other hand, expression of pro-apoptotic genes, such as Bax or Bad, leads to programmed cell death (Aams et al. *Science,* 281:1322-1326 (1998)). The execution of programmed cell death is mediated by caspase-1 related proteinases, including caspase-3, caspase-7, caspase-8 and caspase-9 etc (Thornberry et al. *Science,* 281:1312-1316 (1998)).

The phosphatidylinositol 3'-OH kinase (PI3K)/Akt/PKB pathway appears important for regulating cell survival/cell death (Kulik et al. *Mol. Cell. Biol.* 17:1595-1606 (1997); Franke et al, *Cell,* 88:435-437 (1997); Kauffmann-Zeh et al. *Nature* 385:544-548 (1997) Hemmings Science, 275:628-630 (1997); Dudek et al., *Science,* 275:661-665 (1997)). Survival factors, such as platelet derived growth factor (PDGF), nerve growth factor (NGF) and insulin-like growth factor-1 (IGF-1), promote cell survival under various conditions by inducing the activity of PI3K (Kulik et al. 1997, Hemmings 1997). Activated PI3K leads to the production of phosphatidylinositol (3,4,5)-triphosphate (PtdIns(3,4,5)-P3), which in turn binds to, and promotes the activation of, the serine/threonine kinase Akt, which contains a pleckstrin homology (PH)-domain (Franke et al *Cell,* 81:727-736 (1995); Hemmings *Science,* 277:534 (1997); Downward, *Curr. Opin. Cell Biol.* 10:262-267 (1998), Alessi et al., *EMBO J.* 15: 6541-6551 (1996)). Specific inhibitors of PI3K or dominant negative Akt/PKB mutants abolish survival-promoting activities of these growth factors or cytokines. It has been previously disclosed that inhibitors of PI3K (LY294002 or wortmannin) blocked the activation of Akt/PKB by upstream kinases. In addition, introduction of constitutively active PI3K or Akt/PKB mutants promotes cell survival under conditions in which cells normally undergo apoptotic cell death (Kulik et al. 1997, Dudek et al. 1997).

Analysis of Akt levels in human tumors showed that Akt2 is overexpressed in a significant number of ovarian (J. Q. Cheung et al. *Proc. Natl. Acad. Sci. U.S.A.* 89:9267-9271 (1992)) and pancreatic cancers (J. Q. Cheung et al. *Proc. Natl. Acad. Sci. U.S.A.* 93:3636-3641 (1996)). Similarly, Akt3 was found to be overexpressed in breast and prostate cancer cell lines (Nakatani et al. *J. Biol. Chem.* 274:21528-21532 (1999).

The tumor suppressor PTEN, a protein and lipid phosphatase that specifically removes the 3' phosphate of PtdIns (3,4,5)-P3, is a negative regulator of the PI3K/Akt pathway (Li et al. *Science* 275:1943-1947 (1997), Stambolic et al. *Cell* 95:29-39 (1998), Sun et al. *Proc. Natl. Acad. Sci. U.S.A.* 96:6199-6204 (1999)). Germline mutations of PIEN are responsible for human cancer syndromes such as Cowden disease (Liaw et al. *Nature Genetics* 16:64-67 (1997)). PTEN is deleted in a large percentage of human tumors and tumor cell lines without functional PTEN show elevated levels of activated Akt (Li et al. supra, Guldberg et al. *Cancer Research* 57:3660-3663 (1997), Risinger et al. *Cancer Research* 57:4736-4738 (1997)).

These observations demonstrate that the PI3K/Akt pathway plays important roles for regulating cell survival or apoptosis in tumorigenesis.

Three members of the Akt/PKB subfamily of second-messenger regulated serine/threonine protein kinases have been identified and termed Akt1/PKBα, Akt2/PKBβ, and Akt3/PKBγ, respectively. The isoforms are homologous, particularly in regions encoding the catalytic domains. Akt/PKBs are activated by phosphorylation events occurring in response to PI3K signaling. PI3K phosphorylates membrane inositol phospholipids, generating the second messengers phosphatidyl-inositol 3,4,5-trisphosphate and phosphatidylinositol 3,4-bisphosphate, which have been shown to bind to the PH domain of Akt/PKB. The current model of Akt/PKB activation proposes recruitment of the enzyme to the membrane by 3'-phosphorylated phosphoinositides, where phosphorylation of the regulatory sites of Akt/PKB by the upstream kinases occurs (B. A. Hemmings, *Science* 275:628-630 (1997); B. A. Hemmings, *Science* 276:534 (1997); J. Downward, *Science* 279:673-674 (1998)).

Phosphorylation of Akt1/PKBα occurs on two regulatory sites, $Thr^{308}$ in the catalytic domain activation loop and on $Ser^{473}$ near the carboxy terminus (D. R. Alessi et al. *EMBO J.* 15:6541-6551 (1996) and R. Meier et al. *J. Biol. Chem.* 272: 30491-30497 (1997)). Equivalent regulatory phosphorylation sites occur in Akt2/PKBβ and Akt3/PKBγ. The upstream kinase, which phosphorylates Akt/PKB at the activation loop site has been cloned and termed 3'-phosphoinositide dependent protein kinase 1 (PDK1). PDK1 phosphorylates not only Akt/PKB, but also p70 ribosomal S6 kinase, p90RSK, serum and glucocorticoid-regulated kinase (SGK), and protein kinase C. The upstream kinase phosphorylating the regulatory site of Akt/PKB near the carboxy terminus has not been identified yet, but recent reports imply a role for the integrin-linked kinase (ILK-1), a serine/threonine protein kinase, or autophosphorylation.

Inhibition of Akt activation and activity can be achieved by inhibiting PI3K with inhibitors such as LY294002 and wortmannin. However, PI3K inhibition has the potential to indiscriminately affect not just all three Akt isozymes but also other PH domain-containing signaling molecules that are dependent on PtdIns(3,4,5)-P3, such as the Tec family of tyrosine kinases. Furthermore, it has been disclosed that Akt can be activated by growth signals that are independent of PI3K.

Alternatively, Akt activity can be inhibited by blocking the activity of the upstream kinase PDK1. No specific PDK1 inhibitors have been disclosed. Again, inhibition of PDK1 would result in inhibition of multiple protein kinases whose activities depend on PDK1, such as atypical PKC isoforms, SGK, and S6 kinases (Williams et al. *Curr. Biol.* 10:439-448 (2000).

It is an object of the instant invention to provide novel compounds that are inhibitors of Akt/PKB.

It is also an object of the present invention to provide pharmaceutical compositions that comprise the novel compounds that are inhibitors of Akt/PKB.

It is also an object of the present invention to provide a method for treating cancer that comprises administering such inhibitors of Ak/PKB activity.

SUMMARY OF THE INVENTION

The instant invention provides for compounds which comprise a five-membered heterocyclic ring fused to a substituted pyrazine moiety that inhibit Akt/PKB activity. In particular, the compounds disclosed selectively inhibit one or two of the Akt/PKB isoforms. The invention also provides for compositions comprising such inhibitory compounds and methods of inhibiting Akt/PKB activity by administering the compound to a patient in need of treatment of cancer.

DETAILED DESCRIPTION OF THE INVENTION

The compounds of the instant invention are useful in the inhibition of the activity of the serine/threonine kinase Akt. In a first embodiment of this invention, the inhibitors of Akt activity are illustrated by the formula A:

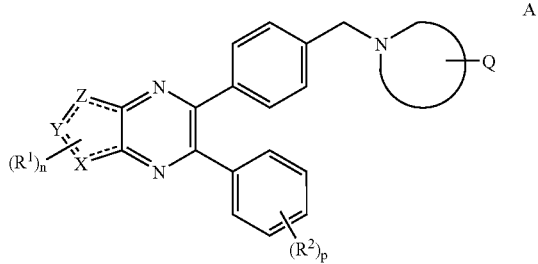

wherein:
n is 0, 1, 2 or 3;
p is 0, 1, 2 or 3;
r is 0 or 1;
s is 0 or 1;
m is 0 or 1;
a is 0 or 1;
b is 0 or 1;
X, Y and Z are independently selected from: C, N, S or O provided that at least one of X, Y or Z is N, S or O;

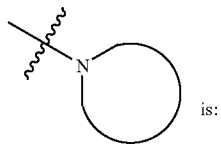 is:

heterocycle, optionally substituted with one to three $R^z$;
Q is selected from: H, $-NR^5R^6$ and heterocycle, said heterocycle which is optionally substituted with one to three $R^z$;
$R^1$ and $R^2$ are independently selected from:
1) $(C=O)_aO_bC_1-C_{10}$ alkyl,
2) $(C=O)_aO_b$ aryl,
3) $C_2-C_{10}$ alkenyl,
4) $C_2-C_{10}$ alkynyl,
5) $(C=O)_aO_b$ heterocyclyl,
6) $(C=O)_aO_bC_3-C_8$ cycloalkyl,
7) $CO_2H$,
8) halo,
9) CN,
10) OH,
11) $O_bC_1-C_6$ perfluoroalkyl,
12) $O_a(C=O)_bNR^3R^4$,
13) $NR^c(C=O)NR^3R^4$,
14) $S(O)_mR^a$,
15) $S(O)_2NR^3R^4$,
16) $NR^cS(O)_mR^a$,
17) oxo,
18) CHO,
19) $NO_2$,
20) $NR^c(C=O)O_bR^a$,
21) $O(C=O)O_bC_1-C_{10}$ alkyl,
22) $O(C=O)O_bC_3-C_8$ cycloalkyl,
23) $O(C=O)O_b$ aryl, and
24) $O(C=O)O_b$-heterocycle,
said alkyl, aryl, alkenyl, alkynyl, heterocyclyl, and cycloalkyl optionally substituted with one or more substituents selected from $R^z$;
$R^3$ and $R^4$ are independently selected from:
1) H,
2) $(C=O)_aO_bC_1-C_{10}$ alkyl,
3) $(C=O)_aO_b$ aryl,
4) $C_2-C_{10}$ alkenyl,
5) $C_2-C_{10}$ alkynyl,
6) $(C=O)_aO_b$ heterocyclyl,
7) $(C=O)_aO_bC_3-C_8$ cycloalkyl,
8) OH,
9) $C_1-C_6$ perfluoroalkyl,
10) $S(O)_mR^a$, and
11) CHO,
said alkyl, cycloalkyl, aryl, heterocylyl, alkenyl, and alkynyl is optionally substituted with one or more substituents selected from $R^z$, or
$R^3$ and $R^4$ can be taken together with the nitrogen to which they are attached to form a monocyclic or bicyclic heterocycle with 4-7 members in each ring and optionally containing, in addition to the nitrogen, 1-3 heteroatoms selected from N, O and S, said monocyclic or bicyclic heterocycle optionally substituted with one or more substituents selected from $R^z$;
$R^5$ and $R^6$ are independently selected from:
1) H,
2) $(C=O)_aO_bC_1-C_{10}$ alkyl,
3) $(C=O)_aO_b$ aryl,
4) $C_2-C_{10}$ alkenyl,
5) $C_2-C_{10}$ alkynyl,
6) $(C=O)_aO_b$ heterocyclyl,
7) $(C=O)_aO_bC_3-C_8$ cycloalkyl,
8) OH,
9) $C_1-C_6$ perfluoroalkyl,
10) $(C=O)NR^3R^4$,
11) $S(O)_mR^a$,
12) $S(O)_2NR^3R^4$, and
13) CHO,
said alkyl, cycloalkyl, aryl, heterocylyl, alkenyl, and alkynyl is optionally substituted with one or more substituents selected from $R^z$, or
$R^5$ and $R^6$ can be taken together with the nitrogen to which they are attached to form a monocyclic or bicyclic heterocycle with 4-7 members in each ring and optionally containing, in addition to the nitrogen, 1-3 heteroatoms selected from N, O and S, said monocyclic or bicyclic heterocycle optionally substituted with one or more substituents selected from $R^z$;

$R^z$ is selected from:
1) $(C=O)_rO_s(C_1-C_{10})$alkyl,
2) $O_r(C_1-C_3)$perfluoroalkyl,
3) $(C_0-C_6)$alkylene-$S(O)_mR^a$,
4) oxo,
5) OH,
6) halo,
7) CN,
8) $(C=O)_rO_s(C_2-C_{10})$alkenyl,
9) $(C=O)_rO_s(C_2-C_{10})$alkynyl,
10) $(C=O)_rO_s(C_3-C_6)$cycloalkyl,
11) $(C=O)_rO_s(C_0-C_6)$alkylene-aryl,
12) $(C=O)_rO_s(C_0-C_6)$alkylene-heterocyclyl,
13) $(C=O)_rO_s(C_0-C_6)$alkylene-$N(R^b)_2$,
14) $C(O)R^a$,
15) $(C_0-C_6)$alkylene-$CO_2R^a$,
16) C(O)H,
17) $(C_0-C_6)$alkylene-$CO_2H$,
18) $C(O)N(R^b)_2$,
19) $S(O)_mR^a$,
20) $NR^c(C=O)O_bR^a$,
21) $O(C=O)O_bC_1-C_{10}$ alkyl,
22) $O(C=O)O_bC_3-C_8$ cycloalkyl,
23) $O(C=O)O_b$ aryl, and
24) $O(C=O)O_b$-heterocycle, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;

$R^a$ is substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_6)$cycloalkyl, substituted or unsubstituted aryl, $(C_1-C_6)$perfluoroalkyl, 2,2,2-trifluoroethyl, or substituted or unsubstituted heterocyclyl; and $R^b$ is H, $(C_1-C_6)$alkyl, substituted or unsubstituted aryl, substituted or unsubstituted benzyl, substituted or unsubstituted heterocyclyl, $(C_3-C_6)$cycloalkyl, $(C=O)OC_1-C_6$ alkyl, $(C=O)C_1-C_6$ alkyl or $S(O)_2R^a$;

$R^c$ is selected from:
1) H,
2) $C_1-C_{10}$ alkyl,
3) aryl,
4) $C_2-C_{10}$ alkenyl,
5) $C_2-C_{10}$ alkynyl,
6) heterocyclyl,
7) $C_3-C_8$ cycloalkyl,
8) $C_1-C_6$ perfluoroalkyl, said alkyl, cycloalkyl, aryl, heterocylyl, alkenyl, and alkynyl is optionally substituted with one or more substituents selected from $R^z$;

or a pharmaceutically acceptable salt or a stereoisomer thereof.

A second embodiment of the instant invention is a compound as illustrated above by formula A, wherein:
n is 0 or 1;

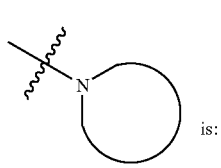

is:

heterocycle selected from 2-azepinone, benzimidazolyl, benzimidazolonyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl, said heterocycle optionally substituted with one to three $R^z$;

Q is selected from: H and $—NR^5R^6$;

$R^1$ and $R^2$ are independently selected from:
1) $(C=O)_aO_bC_1-C_{10}$ alkyl,
2) $(C=O)_aO_b$ aryl,
3) $C_2-C_{10}$ alkenyl,
4) $C_2-C_{10}$ alkynyl,
5) $(C=O)_aO_b$ heterocyclyl,
6) $(C=O)_aO_bC_3-C_8$ cycloalkyl,
7) $CO_2H$,
8) halo,
9) CN,
10) OH,
11) $O_bC_1-C_6$ perfluoroalkyl,
12) $S(O)_mR^a$,
13) $NR^cS(O)_mR^a$,
14) oxo,
15) CHO,
16) $NO_2$,
17) $NR^c(C=O)O_bR^a$,
18) $O(C=O)O_bC_1-C_{10}$ alkyl,
19) $O(C=O)O_bC_3-C_8$ cycloalkyl,
20) $O(C=O)O_b$ aryl,
21) $O(C=O)O_b$-heterocycle, and
22) $NH_2$, said alkyl, aryl, alkenyl, alkynyl, heterocyclyl, and cycloalkyl optionally substituted with one or more substituents selected from $R^z$;

and all other substituents and variables are as defined in the first embodiment;

or a pharmaceutically acceptable salt or a stereoisomer thereof.

A third embodiment of the instant invention is a compound as illustrated above by formula A wherein:

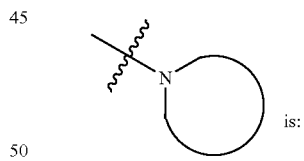

is:

heterocycle selected from

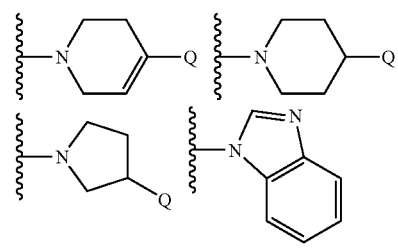

said heterocycle optionally substituted with one to three $R^z$;

Q is selected from: $—NR^5R^6$;

R⁵ and R⁶ are independently selected from:
1) H,
2) (C=O)$_a$O$_b$C$_1$-C$_{10}$ alkyl,
3) (C=O)$_a$O$_b$ aryl,
4) C$_2$-C$_{10}$ alkenyl,
5) C$_2$-C$_{10}$ alkynyl,
6) (C=O)$_a$O$_b$ heterocyclyl,
7) (C=O)$_a$O$_b$C$_3$-C$_8$ cycloalkyl,
8) OH,
9) C$_1$-C$_6$ perfluoroalkyl,
10) S(O)$_m$R$^a$, and
11) CHO,
said alkyl, cycloalkyl, aryl, heterocylyl, alkenyl, and alkynyl is optionally substituted with one or more substituents selected from R$^z$, or
R⁵ and R⁶ can be taken together with the nitrogen to which they are attached to form a monocyclic or bicyclic heterocycle with 4-7 members in each ring and optionally containing, in addition to the nitrogen, 1-3 heteroatoms selected from N, O and S, said monocyclic or bicyclic heterocycle optionally substituted with one or more substituents selected from R$^z$;
and all other substitutents and variables are as defined in the second embodiment;
or a pharmaceutically acceptable salt or a stereoisomer thereof.

A fourth embodiment of the instant invention is a compound as illustrated above by formula A wherein:
Q is selected from:

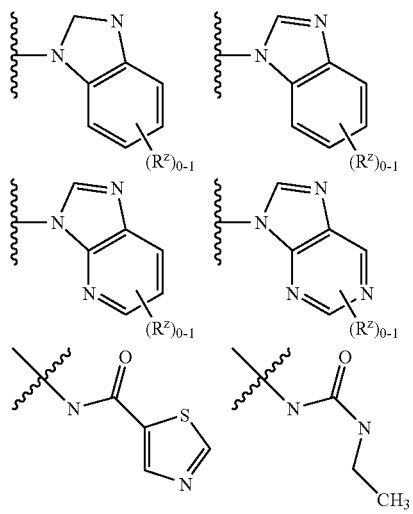

wherein R$^z$ can attach anywhere on the bicyclic structure;
R¹ and R² are independently selected from:
1) (C$_1$-C$_6$)alkyl,
2) (C$_1$-C$_{10}$)alkyl-OH
3) CO$_2$H,
4) halo,
5) CN,
6) OH,
7) oxo,
8) CHO,
9) NO$_2$, and
10) NH$_2$
R$^z$ is independently selected from:
1) (C$_1$-C$_6$)alkyl,
2) (C$_1$-C$_{10}$)alkyl-OH 3) CO$_2$H,
4) halo,
5) CN,
6) OH,
7) oxo,
8) CHO,
9) NO$_2$, and
10) NH$_2$
and all other substituents and variables are as defined in the third embodiment;
or a pharmaceutically acceptable salt or a stereoisomer thereof.

Specific compounds of the instant invention include:
1-{1-[4-(3-phenylthieno[3,4-b]pyrazin-2-yl)benzyl]piperidin-4-yl}-1,3-dihydro-2H-benzimidazol-2-one;
N-ethyl-N'-{(3R)-1-[4-(3-phenylthieno[3,4-b]pyrazin-2-yl)benzyl]pyrrolidin-3-yl}urea;
N-{(3R)-1-[4-(3-phenylthieno[3,4-b]pyrazin-2-yl)benzyl]pyrrolidin-3-yl}-1,3-thiazole-5-carboxamide;
9-{1-[4-(3-phenylthieno[3,4-b]pyrazin-2-yl)benzyl]piperidin-4-yl}-9H-purin-6-amine;
2-(4-{[4-(3H-imidazo[4,5-b]pyridin-3-yl)piperidin-1-yl]methyl}phenyl)-3-phenylthieno[3,4-b]pyrazine;
9-{1-[4-(3-phenylthieno[3,4-b]pyrazin-2-yl)benzyl]piperidin-4-yl}-9H-purine;
{1-[4-(3-phenylthieno[3,4-b]pyrazin-2-yl)benzyl]-1H-benzimidazol-2-yl}methanol;
2-{4-[(2-methyl-1H-benzimidazol-1-yl)methyl]phenyl}-3-phenylthieno[3,4-b]pyrazine;
1-{1-[4-(3-phenylthieno[3,4-b]pyrazin-2-yl)benzyl]-1,2,3,6-tetrahydropyridin-4-yl}-1,3-dihydro-2H-benzimidazol-2-one;
N-{(3R)-1-[4-(3-hydroxy-5-phenyl-2H-pyrazolo[3,4-b]pyrazin-6-yl)benzyl]pyrrolidin-3-yl}-1,3-thiazole-5-carboxamide; and
1-{1-[4-(3-hydroxy-5-phenyl-2H-pyrazolo[3,4-b]pyrazin-6-yl)benzyl]piperidin-4-yl}-1,3-dihydro-2H-benzimidazol-2-one;

or a pharmaceutically acceptable salt or a stereoisomer thereof.

Specific TFA salts of the compounds of the instant invention include:
1-{1-[4-(3-phenylthieno[3,4-b]pyrazin-2-yl)benzyl]piperidin-4-yl}-1,3-dihydro-2H-benzimidazol-2-one;
N-ethyl-N'-{(3R)-1-[4-(3-phenylthieno[3,4-b]pyrazin-2-yl)benzyl]pyrrolidin-3-yl}urea;
N-{(3R)-1-[4-(3-phenylthieno[3,4-b]pyrazin-2-yl)benzyl]pyrrolidin-3-yl}-1,3-thiazole-5-carboxamide;
9-{1-[4-(3-phenylthieno[3,4-b]pyrazin-2-yl)benzyl]piperidin-4-yl}-9H-purin-6-amine;
2-(4-{[4-(3H-imidazo[4,5-b]pyridin-3-yl)piperidin-1-yl]methyl}phenyl)-3-phenylthieno[3,4-b]pyrazine;
9-{1-[4-(3-phenylthieno[3,4-b]pyrazin-2-yl)benzyl]piperidin-4-yl}-9H-purine;
{1-[4-(3-phenylthieno[3,4-b]pyrazin-2-yl)benzyl]-1H-benzimidazol-2-yl}methanol;
2-{4-[(2-methyl-1H-benzimidazol-1-yl)methyl]phenyl}-3-phenylthieno[3,4-b]pyrazine;
1-{1-[4-(3-phenylthieno[3,4-b]pyrazin-2-yl)benzyl]-1,2,3,6-tetrahydropyridin-4-yl}-1,3-dihydro-2H-benzimidazol-2-one;
N-{(3R)-1-[4-(3-hydroxy-5-phenyl-2H-pyrazolo[3,4-b]pyrazin-6-yl)benzyl]pyrrolidin-3-yl}-1,3-thiazole-5-carboxamide; and 1-{1-[4-(3-hydroxy-5-phenyl-2H-pyrazolo[3,4-b]pyrazin-6-yl)benzyl]piperidin-4-yl}-1,3-dihydro-2H-benzimidazol-2-one;

or a stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof. The two tautomeric forms of the benzimidazolonyl moiety are also within the scope of the instant invention.

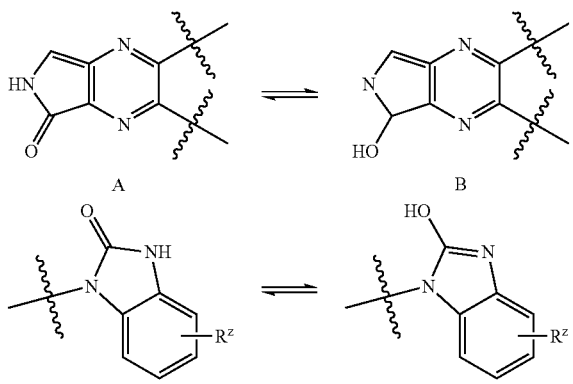

When any variable (e.g. $R^1$, $R^2$, $R^z$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring; respectively. Such heteroaryl moieties for substituent Q include but are not limited to: 2-benzimidazolyl, 2-quinolinyl, 3-quinolinyl, 4-quinolinyl, 1-isoquinolinyl, 3-isoquinolinyl and 4-isoquinolinyl.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, heterocycle is 2-azepinone, benzimidazolyl, benzimidazolonyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

As appreciated by those of skill in the art, "halo" or "halogen" as used herein is intended to include chloro, fluoro, bromo and iodo.

As used herein, unless otherwise specifically defined, substituted alkyl, substituted cycloalkyl, substituted aroyl, substituted aryl, substituted heteroaroyl, substituted heteroaryl, substituted arylsulfonyl, substituted heteroaryl-sulfonyl and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1-C_6$ alkyl$)_2$, $NO_2$, CN, $(C_1-C_6$ alkyl)O—, (aryl)O—, —OH, $(C_1-C_6$ alkyl)$S(O)_m$—, $(C_1-C_6$ alkyl)C(O)NH—, $H_2N$—C(NH)—, $(C_1-C_6$ alkyl)C(O)—, $(C_1-C_6$ alkyl)OC(O)—, $(C_1-C_6$ alkyl)OC(O)NH—, phenyl, pyridyl, imidazolyl, oxazolyl, isoxazolyl, thiazolyl, thienyl, furyl, isothiazolyl and $C_1-C_{20}$ alkyl. For example, a $(C_1-C_6)$alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —(C=O)CH$_2$CH(OH)CH$_3$, —(C=O)OH, —CH$_2$(OH)CH$_2$CH(O), and so on.

The moiety illustrated by the formula:

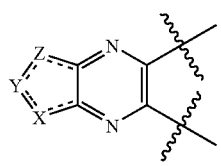

includes the following structures, which are meant to be merely illustrative and not limiting:

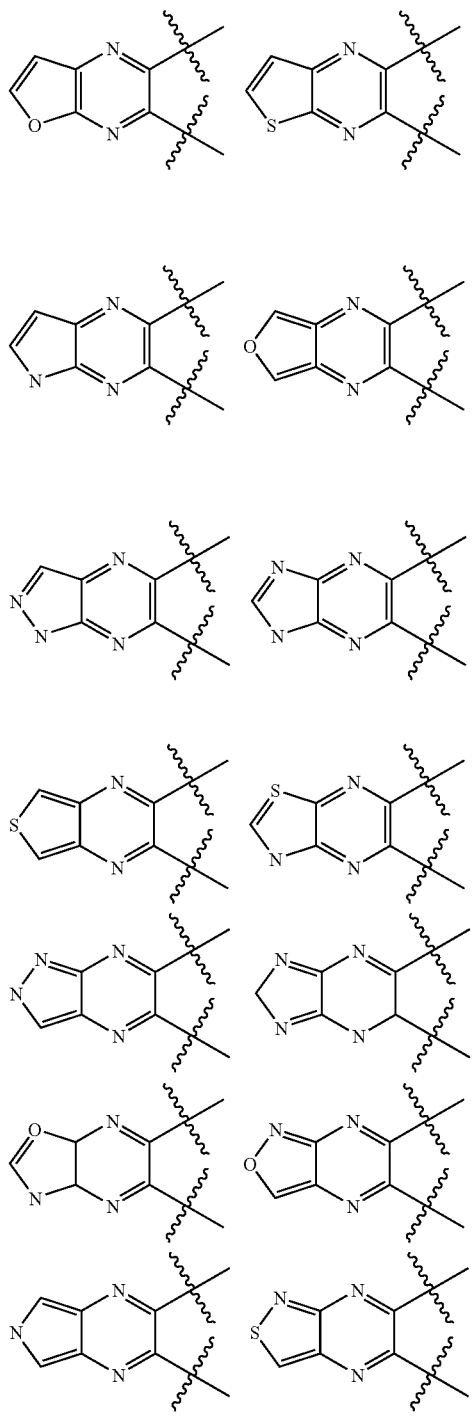

In another embodiment, the moiety illustrated by the formula:

is selected from:

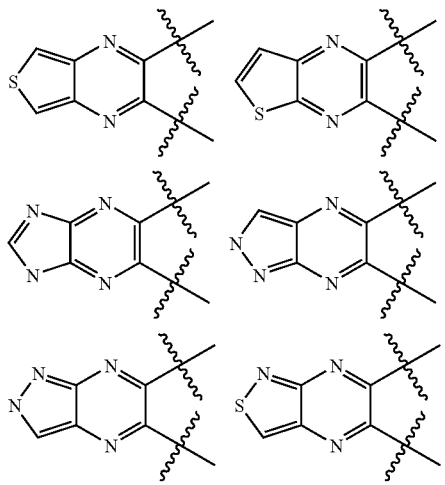

The moieties formed when $R^1$ is oxo include the following structures, which are meant to be merely illustrative and not limiting:

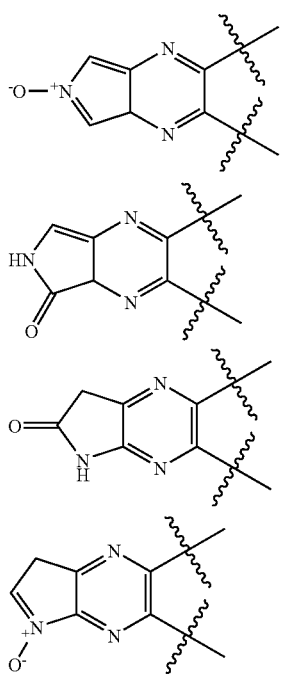

In certain instances, $R^3$ and $R^4$ and $R^5$ and $R^6$ are defined such that they can be taken together with the nitrogen to which they are attached to form a monocyclic or bicyclic heterocycle with 4-7 members in each ring and optionally containing, in addition to the nitrogen, 1-3 additional heteroatoms selected from N, O and S, said heterocycle optionally substituted with one or more substituents selected from $R^z$. Examples of the heterocycles that can thus be formed include, but are not limited to the following, keeping in mind that the heterocycle is optionally substituted with one or more (and preferably one, two or three) substituents chosen from $R^z$:

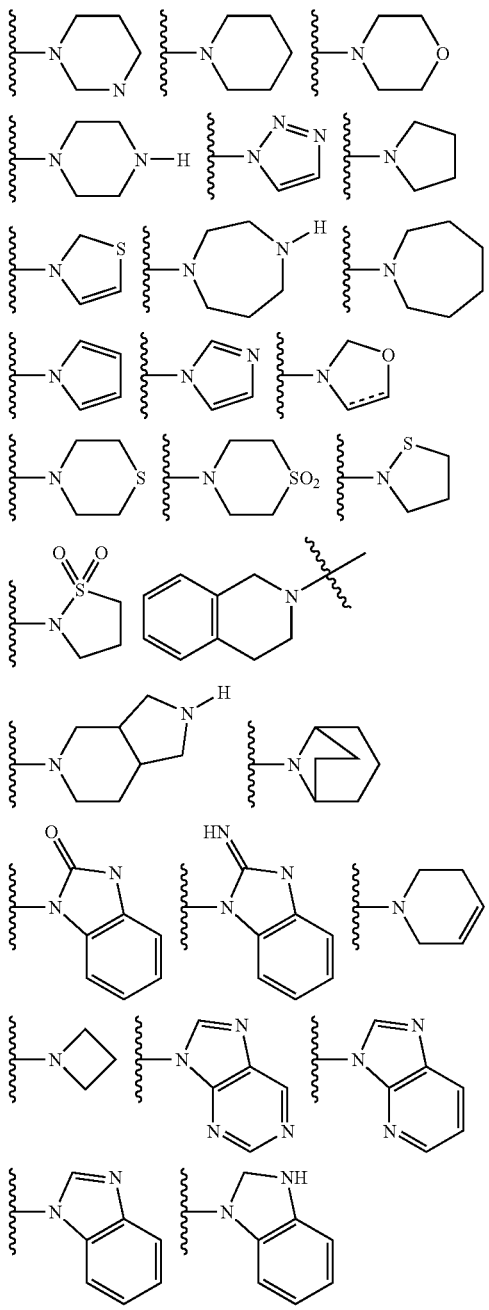

In another embodiment, n is 0 or 1.
In another embodiment, p is 0 or 1.
In another embodiment,

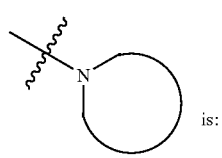

is:

heterocycle selected from

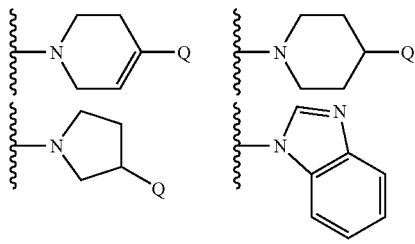

said heterocycle optionally substituted with one to three $R^z$;
In another embodiment, Q is selected from:

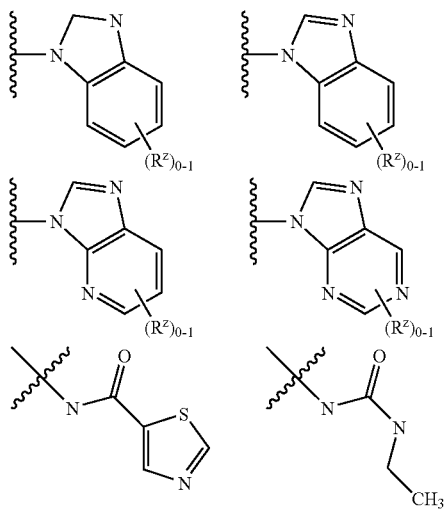

wherein $R^z$ can attach anywhere on the bicyclic structure.

In another embodiment, $R^1$ and $R^2$ are $(C_1-C_6)$alkyl, (C1-C10)alkyl-OH, $CO_2H$, halo, CN, OH, oxo, CHO, $NO_2$, and $NH_2$.

In another embodiment, $R^z$ is oxo, halo, $(C_1-C_6)$alkyl-OH and $NH_2$.

Included in the instant invention is the free form of compounds of formula A, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of Formula A. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the instant invention are inhibitors of the activity of Akt and are thus useful in the treatment of cancer, in particular cancers associated with irregularities in the activity of Akt and/or GSK3. Such cancers include, but are not limited to ovarian, pancreatic and breast cancer.

In an embodiment of the invention, the instant compound is a selective inhibitor whose inhibitory efficacy is dependent on the PH domain. In this embodiment, the compound exhibits a decrease in in vitro inhibitory activity or no in vitro inhibitory activity against truncated Akt proteins lacking the PH domain.

In a further embodiment, the instant compound is selected from the group of a selective inhibitor of Akt1, a selective inhibitor of Akt2 and a selective inhibitor of both Akt1 and Akt2.

In another embodiment, the instant compound is selected from the group of a selective inhibitor of Akt1, a selective inhibitor of Akt2, a selective inhibitor of Akt3 and a selective inhibitor of two of the three Akt isoforms.

In another embodiment, the instant compound is a selective inhibitor of all three Akt isoforms, but is not an inhibitor of one, two or all of such Akt isoforms that have been modified to delete the PH domain, the hinge region or both the PH domain and the hinge region.

The present invention is further directed to a method of inhibiting Akt activity which comprises administering to a mammal in need thereof a pharmaceutically effective amount of the instant compound.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable nonirritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

As used herein, the term "composition" is intended to encompass a product comprising the specified ingredients in the specific amounts, as well as any product which results, directly or indirectly, from combination of the specific ingredients in the specified amounts.

Additionally, the compounds of the instant invention may be administered to a mammal in need thereof using a gel extrusion mechanism (GEM) device, such as that described in U.S. Pat. No. 4,976,697, filed on Dec. 11, 1990, which is hereby incorporated by reference.

The instant compounds may also be co-administered with other well known therapeutic agents that are selected for their particular usefulness against the condition that is being treated.

For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, anti-metabolites; biological response modifiers; hormonal/anti-hormonal therapeutic agents, haematopoietic growth factors, monoclonal antibody targeted therapeutic agents and topoisomerase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans,trans,trans)-bis-mu-(hexane-1,6-diamine)-mu-[diamine-platinum (II)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, iminotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H, 12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNPl350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexahydrofuro(3', 4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768 and WO 01/98278, and pending U.S. Ser. Nos. 60/338,779 (filed Dec. 6, 2001), 60/338,344 (filed Dec. 6, 2001), 60/338,383 (filed Dec. 6, 2001), 60/338,380 (filed Dec. 6, 2001), 60/338,379 (filed Dec. 6, 2001) and 60/344,453 (filed Nov. 7, 2001).

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N-4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-COA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

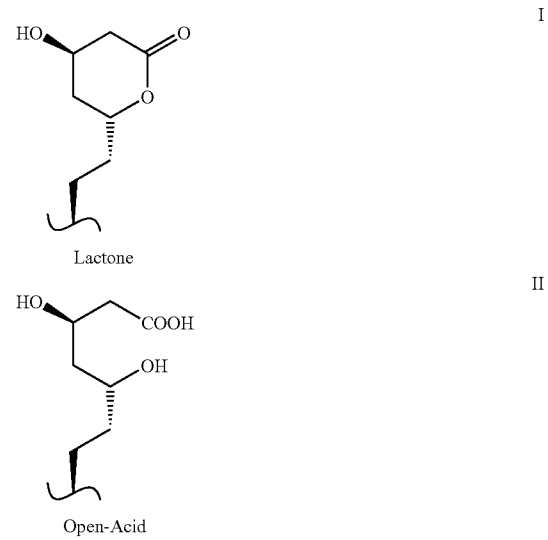

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also, called Rab GGPTase). Examples of prenyl-protein transferase inhibiting compounds include (±)-6-[amino(4-chlorophenyl)(1-methyl-1H-imidazol-5-yl) methyl]-4-(3-chlorophenyl)-1-methyl-2 (1H)-quinolinone, (−)-6-[amino(4-chlorophenyl)(1-methyl-1H-imidazol-5-yl) methyl]-4-(3-chlorophenyl)-1-methyl-2 (1H)-quinolinone, (+)-6-[amino(4-chlorophenyl)(1-methyl-1H-imidazol-5-yl) methyl]-4-(3-chlorophenyl)-1-methyl-2 (1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl) 4-[1-(4-cyanobenzyl)-5-imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl) 4-[1-(4-cyanobenzyl)-2-methyl-5-midazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxaazacyclononadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacycloeicosine-9-carbonitrile, and (+)-19,20-dihydro-3-methyl-19-oxo-5H-18,21-ethano-12,14-etheno-6,10-metheno-22H-benzo [d-]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95110515, WO 95/10516, WO 95/24612, WO 95134535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin 1I antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Inhibitors of COX-2 that are particularly useful in the instant method of treatment are:
3-phenyl-4-(4-(methylsulfonyl)phenyl)-2-(5H)-furanone; and

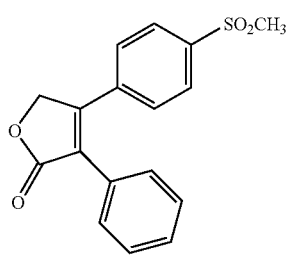

5-chloro-3-(4-methylsulfonyl)phenyl-2-(2-methyl-5-pyridinyl)pyridine;

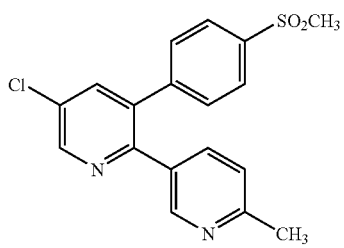

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

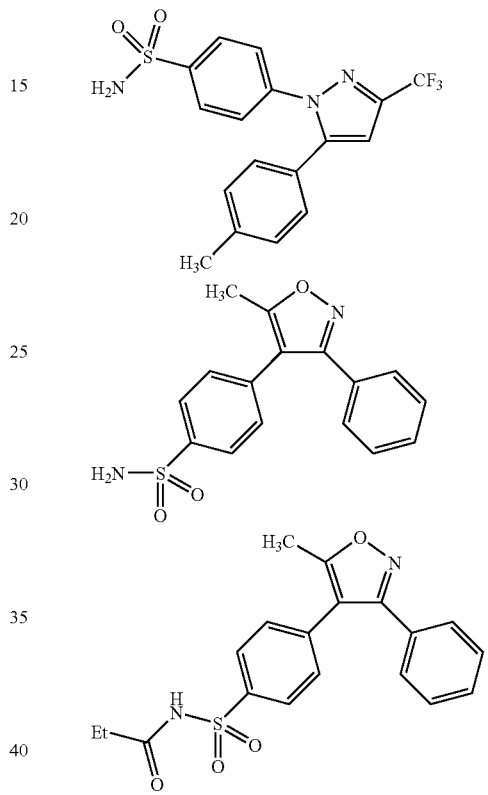

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, ST1571, CEP2563, 4-(3-chlorophenylamino)-5,6-dimethyl-7H-pyrrolo [2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; J. Biol. Chem. 1999;274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthalmol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (Am J Hum Genet 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998;5(8):1105-13), and interferon gamma (J Immunol 2000;164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. For the treatment or prevention of emesis that may result upon administration of the instant compounds, conjunctive therapy with an anti-emesis agent selected from a neurokinin-1 receptor antagonist, a 5HT3 receptor antagonist and a corticosteroid is preferred.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96105193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

A neurokinin-1 receptor antagonist for use in conjunction with the compounds of the present invention is 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

Thus, the scope of the instant invention encompasses the use of the instantly claimed compounds in combination with a second compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor,
10) an angiogenesis inhibitor,
11) an inhibitor of inherent multidrug resistance,
12) an anti-emetic agent,
13) an agent useful in the treatment of anemia,
14) agent useful in the treatment of neutropenia, and
15) an immunologic-enhancing drug.

Also included in the scope of the claims is a method of treating cancer that comprises administering a therapeutically effective amount of a compound of formula A in combination with radiation therapy and/or in combination with a compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor,
10) an angiogenesis inhibitor,
11) an inhibitor of inherent multidrug resistance,
12) an anti-emetic agent,
13) an agent useful in the treatment of anemia,
14) agent useful in the treatment of neutropenia, and
15) an immunologic-enhancing drug.

When a composition according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of an inhibitor of Akt/PKB is administered to a mammal undergoing treatment for cancer. Administration occurs in an amount of inhibitor of between about 0.1 mg/kg of body weight to about 60 mg/kg of body weight per day, preferably of between 0.5 mg/kg of body weight to about 40 mg/kg of body weight per day. A particular therapeutic dosage that comprises the instant composition includes from about 0.01 mg to about 1000 mg of inhibitor of Akt/PKB. Preferably, the dosage comprises from about 1 mg to about 1000 mg of inhibitor of Akt/PKB.

All patents, publications and pending patent applications identified are hereby incorporated by reference.

Abbreviations used in the description of the chemistry and in the Examples that follow are:
DMSO dimethyl sulfoxide
EtOH ethanol
HOAc acetic acid
MeOH methanol
NBS N-bromosuccinamide
PS-DIEA polystyrene diisopropylethylamine;
TIF tetrahydrofuran;
TFA trifluoroacteic acid.

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of formula A hereinabove.

Reactions used to generate the compounds of this invention are prepared by employing reactions as shown in the Reaction Schemes I-II, in addition to other standard manipulations such as ester hydrolysis, cleavage of protecting groups, etc., as may be known in the literature or exemplified in the experimental procedures.

These reactions may be employed in a linear sequence to provide the compounds of the invention or they may be used to synthesize fragments which are subsequently joined by the alkylation reactions described in the Reaction Schemes.

Synopsis of Reaction Schemes:

The requisite intermediates are in some cases commercially available, or can be prepared according to literature procedures. As illustrated in Reaction Scheme I, a suitably substituted phenylacetylide may be reacted with copper iodide to form the corresponding copper acetylide I-1 (see for example, Sonogashira, K.; Toda, Y.; Hagihara, N. *Tetrahedron Lett.* 1975, 4467). Intermediate I-1 may then react with a suitably substituted electrophilic phenyl moiety to provide the asymetrically substituted diphenyl acetylene I-2. Reaction with NBS followed by hydrolysis provides the substituted benzil I-3 (see for example, Yusybov, M. S.; Filimonov, V. D.; *Synthesis* 1991, 2:131). A variety of substituted and unsubstituted benzils may also be obtained commercially.

Reaction Scheme II illustrates the preparation of the compounds of the instant invention, starting with a suitably substituted bromomethylbenzil II-1. This intermediate can be reacted with a suitable amine to provide intermediate II-2, which can be reacted with a suitable heterocyclic diamine to provide a regioisomeric mixture of pyrazinyl instant compounds, which can usually be separated chromatagraphically.

In Reaction Scheme III, the heterocyclic diamine is thiophene-3,4-diamine (commercially available from Lancaster).

In Reaction Scheme IV, the heterocyclic diamine is furan-3,4-diamine (see for example, Yu, Hai Quan; Liu, Yong Jun; Peng, Da Cheng; Liu, Cheng Bu; *Chinese Chemical Letters* 1999, 10:937-940).

In Reaction Scheme V, the heterocyclic diamine is 3,4-diamino-1H-pyrazol-5-ol.

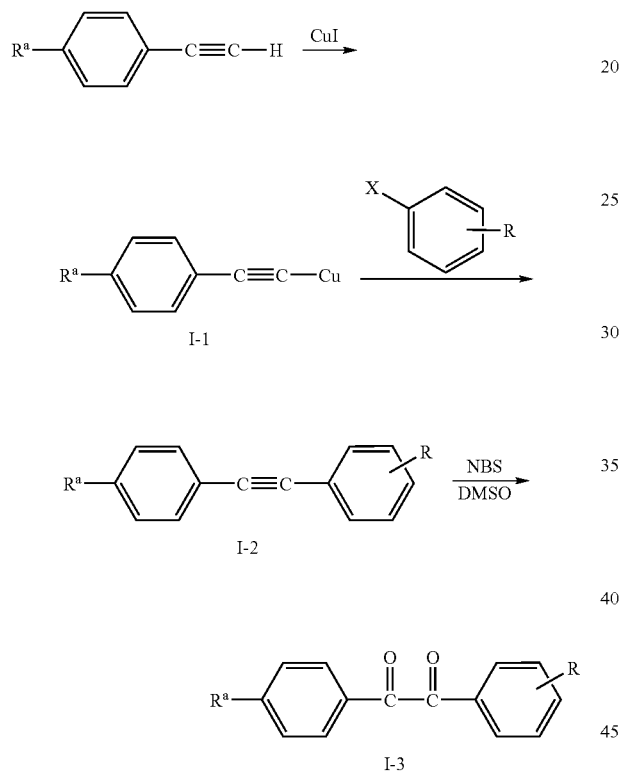

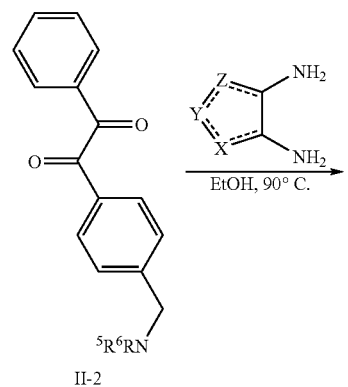

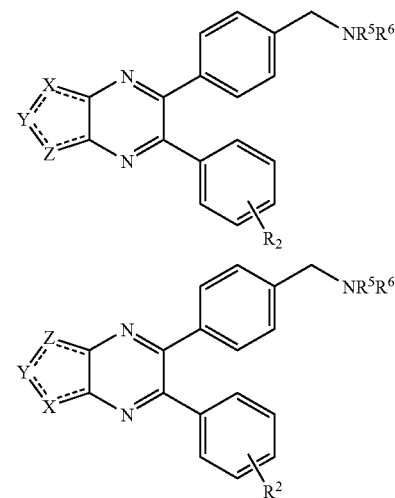

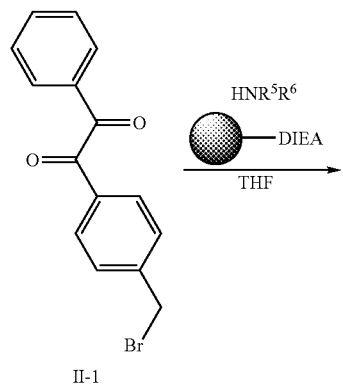

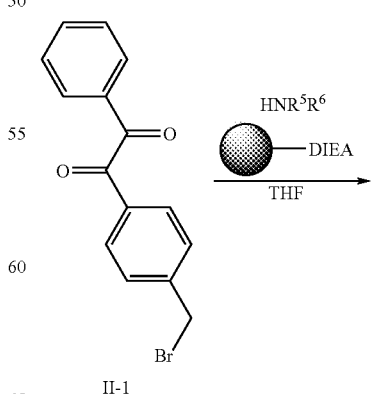

-continued
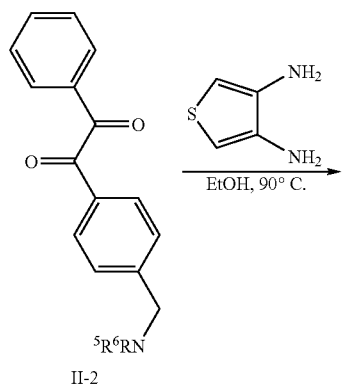
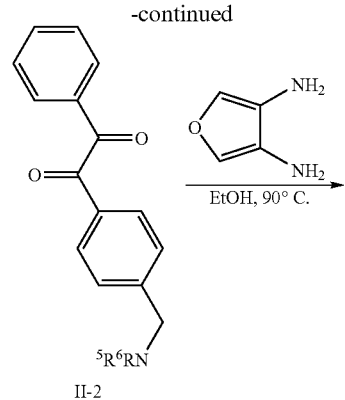
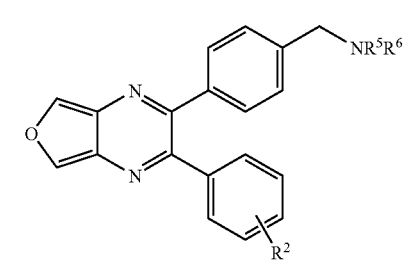
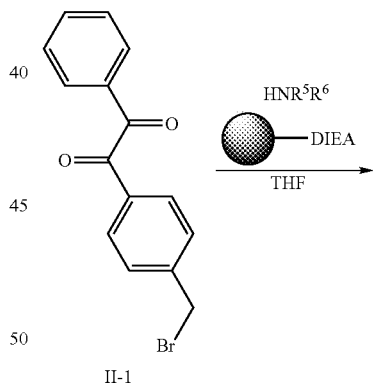
Reaction Scheme V
Reaction Scheme IV
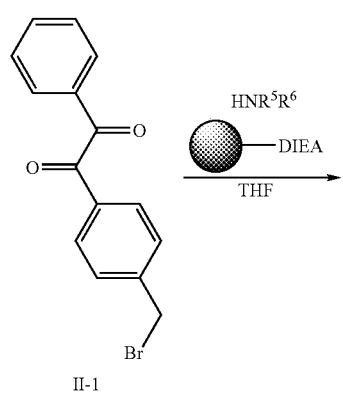
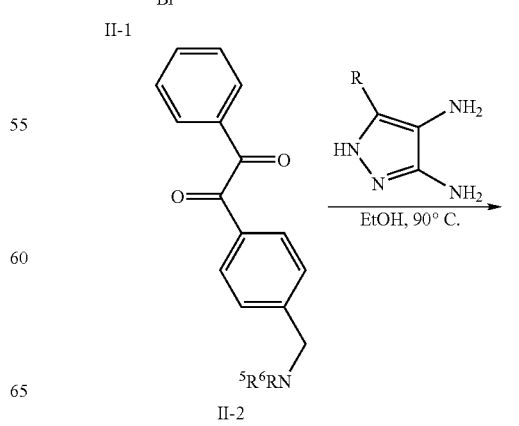

EXAMPLES

Examples provided are intended to assist in a further understanding of the invention. Particular materials employed, species and conditions are intended to be further illustrative of the invention and not limitative of the reasonable scope thereof.

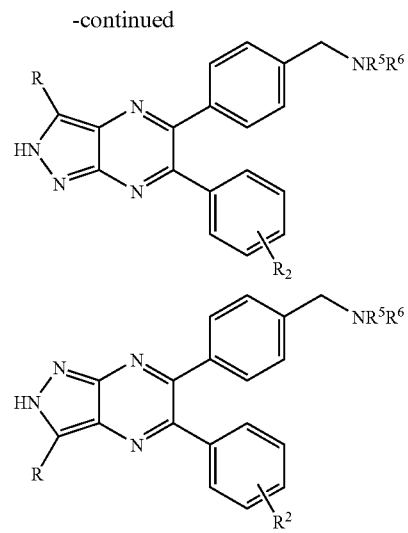

1-(4-{[4-(2-Oxo-2,3-dihydro-1H-benzimidazol-1-yl)pipepridin-1-yl]methyl}phenyl) 2-phenylethane-1,2-dione (1-3)

To an 8 mL vial was placed bromomethyl benzil 1-1 (Toronto Research Chemicals, 500 mg, 1.65 mmol), 4-(2-keto-1-benzimidazolinyl)piperidine 1-2 (Aldrich, 358 mg, 1.65 mol), PS-DIEA (887 mg, 3.3 mmol, 3.72 mm/g) and dry THF (6 mL, 0.3 M). The vial was placed on a GlasCol rotator and allowed to rotate for 2 hours. After this time, the contents of the vial were filtered through a 10 mL BioRad tube, washed with THF and concentrated in vaccuo. The crude material was then purified on an Agilent 1100 series Mass Guided HPLC purification system to afford the TFA salt of 1-3 as a pale yellow solid. Analytical LCMS: single peak (214 nm) at 2.487 min ($CH_3CN/H_2O/1\%$ TFA, 4 min gradient), M+1. $^1$H NMR (500 MHz, DMSO-$d_6$): δ 10.9 (s, 1H), 8.05 (m, 2H), 7.93 (m, 2H), 7.79 (m, 2H), 7.63 (m, 2H), 7.24 (s, 1H), 6.98 (s, 4H), 4.47 ((s, 2H), 3.5 (m, 2H), 3.2 (m, 3H), 2.61 (q, J=1 Hz, 2H), 1.9 (d, J=11 Hz, 2H). HRMS, calc'd for $C_{27}H_{26}N_3O_3$ (M+H), 440.1965; found 440.1968.

1-{1-[4-(3-phenylthieno[3,4-b]pyrazin-2-yl)benzyl]piperidin-4-yl}-1,3-dihydro-2H-benzimidazol-2-one (14)

1-(4-{[4-(2-oxo-2,3-dihydro-1H-benzimidazol-1-yl)pipepridin-1-yl]methyl}phenyl)-2-phenylethane-1,2-dione (1-3 44 mg, 0.1 mmol), and 3,4-diaminothiophene dihydrochloride (22 mg, 0.12 mmol) were dissolved in 2 mL of MeOH/HOAc (9/1) in an 8 mL vial. The solution was stirred at room temperature for 3 hours. After this time, the reaction was concentrated in vaccuo. The crude material was then purified on an Agilent 1100 series Mass Guided HPLC purification system to afford the TFA salt of 14 as a brown solid. Analytical LCMS: single peak (214 nm) at 2.452 min ($CH_3CN/H_2O/1\%$ TFA, 4 min gradient), M+1 peak m/e 518.2. $^1$H NMR (500 MHz, DMSO-$d_6$): δ 10.93 (s, 1H), δ 10.80 (s, 10H), 8.42 (d, J=3.1 Hz, 1H), 8.45 (d, J=3.1 Hz, 1H), 7.60 (d, J=8.5 Hz, 2H), 7.50-7.53 (m, 3H), 7.34-7.42 (m, 5H), 6.99-7.01 (m, 3H), 4.53 (d, J=5.3 Hz, 2H), 3.36-3.48 (m, 2H), 3.17 (q, J=12.1 Hz, 1H), 2.8 (q, J=13.4 Hz, 2H), 1.91 (d, J=13.2 Hz, 2H). HRMS, calc'd for $C_{31}H_{28}N_5OS$ (M+H), 518.2009; found 518.2001.

Compounds in Table 1 were synthesized as shown in Scheme 1, but substituting the appropriately substituted cyclic amine for compound 1-2 in Scheme 1, or the appropriately substituted aromatic diamine for the 3,4-diaminothiophene in Reaction Schemes 1 and 2: Unless otherwise stated, the TFA salt of the compound shown was isolated by Mass Guided HPLC purification.

TABLE 1

| Nomenclature | Compound | MS M + 1 |
|---|---|---|
| 1-{1-[4-(3-phenylthieno[3,4-b]pyrazin-2-yl)benzyl]piperidin-4-yl}-1,3-dihydro-2H-benzimidazol-2-one | 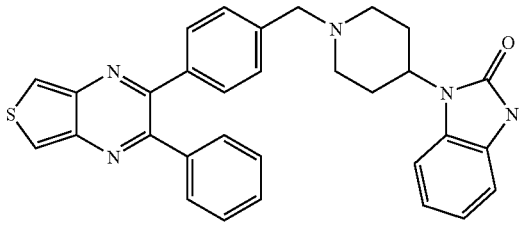 | 518.2 |
| N-ethyl-N'-{(3R)-1-[4-(3-phenylthieno[3,4-b]pyrazin-2-yl)benzyl]pyrrolidin-3-yl}urea | 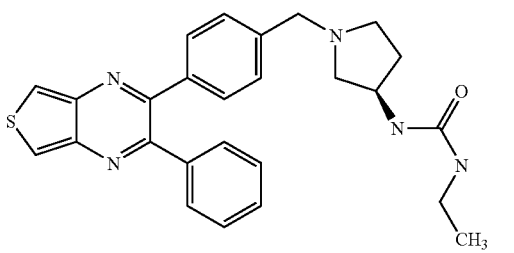 | 458.2 |
| N-{(3R)-1-[4-(3-phenylthieno[3,4-b]pyrazin-2-yl)benzyl]pyrrolidin-3-yl}-1,3-thiazole-5-carboxamide | 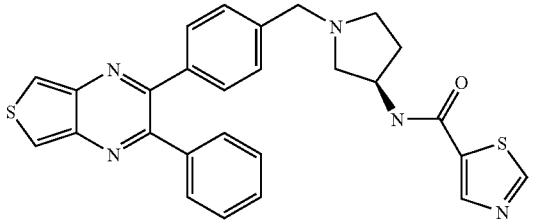 | 498.1 |
| 9-{1-[4-(3-phenylthieno[3,4-b]pyrazin-2-yl)benzyl]piperidin-4-yl}-9H-purine | 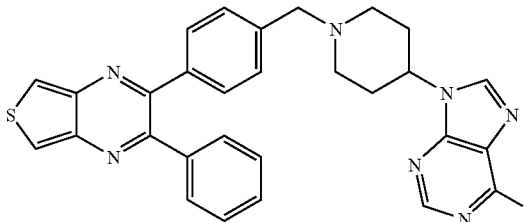 | 519.2 |
| 2-{4-[(2-methyl-1H-benzimidazol-1-yl)methyl]phenyl}-3-phenylthieno[3,4-b]pyrazine | 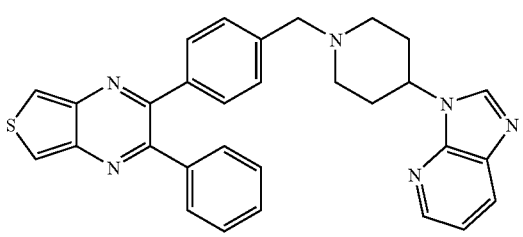 | 503.2 |
| 9-{1-[4-(3-phenylthieno[3,4-b]pyrazin-2-yl)benzyl]piperidin-4-yl}-9H-purine | 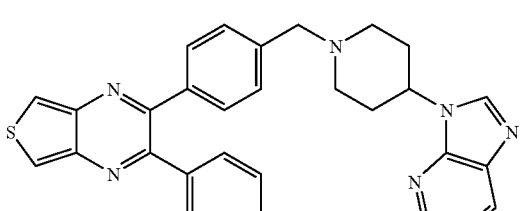 | 504.2 |

TABLE 1-continued

| Nomenclature | Compound | MS M + 1 |
|---|---|---|
| {1-[4-(3-phenylthieno[3,4-b]pyrazin-2-yl)benzyl]-1H-benzimidazol-2-yl}methanol | | 449.1 |
| 2-{4-[(2-methyl-1H-benzimidazol-1-yl)methyl]phenyl}-3-phenylthieno[3,4-b]pyrazine | | 433.1 |
| 1-{1-[4-(3-phenylthieno[3,4-b]pyrazin-2-yl)benzyl]-1,2,3,6-tetrahydropyridin-4-yl}-1,3-dihydro-2H-benzimidazol-2-one | | 516.2 |
| N-{(3R)-1-[4-(3-hydroxy-5-phenyl-2H-pyrazolo[3,4-b]pyrazin-6-yl)benzyl]pyrrolidin-3-yl}-1,3-thiazole-5-carboxamide | | 498.2 |
| 1-{1-[4-(3-hydroxy-5-phenyl-2H-pyrazolo[3,4-b]pyrazin-6-yl)benzyl]piperidin-4-yl}-1,3-dihydro-2H-benzimidazol-2-one | | 518.2 |

Example 1

Cloning of the Human Akt Isoforms and ΔPH-Akt1

The pS2neo vector (deposited in the ATCC on Apr. 3, 2001 as ATCC PTA-3253) was prepared as follows: The pRmHA3 vector (prepared as described in *Nucl. Acid Res.* 16:1043-1061 (1988)) was cut with BglII and a 2734 bp fragment was isolated. The pUChsneo vector (prepared as described in EMBO J. 4:167-171 (1985)) was also cut with BglII and a 4029 bp band was isolated. These two isolated fragments were ligated together to generate a vector termed pS2neo-1. This plasmid contains a polylinker between a metallothionine promoter and an alcohol dehydrogenase poly A addition site. It also has a neo resistance gene driven by a heat shock promoter. The pS2neo-1 vector was cut with Psp5II and BsiWI. Two complementary oligonucleotides were synthesized and then annealed (CTGCGGCCGC (SEQ.ID.NO.: 1) and GTACGCGGCCGCAG (SEQ.ID.NO.: 2)).

The cut pS2neo-1 and the annealed oligonucleotides were ligated together to generate a second vector, pS2neo. Added in this conversion was a NotI site to aid in the linearization prior to transfection into S2 cells.

Human Akt1 gene was amplified by PCR (Clontech) out of a human spleen cDNA (Clontech) using the 5' primer: 5' CGCGAATTCAGATCTACCATGAGC-GACGTGGCTATTGTG 3' (SEQ.ID.NO.: 3), and the 3' primer: 5' CGCTCTAGAGGATCCTCAGGCCGTGCT-GCTGGC 3' (SEQ.ID.NO.: 4). The 5' primer included an EcoRI and BglII site. The 3' primer included an XbaI and BamHI site for cloning purposes. The resultant PCR product was subcloned into pGEM3Z (Promega) as an EcoRI/XbaI fragment. For expression/purification purposes, a middle T tag was added to the 5'end of the full length' Akt1 gene using the PCR primer: 5' GTACGATGCTGAACGATATCTTCG 3' (SEQ.ID.NO.: 5). The resulting PCR product encompassed a 5' KpnI site and a 3' BamHI site which were used to subclone the fragment in frame with a biotin tag containing insect cell expression vector, pS2neo.

For the expression of a pleckstrin homology domain (PH) deleted (Aaa 4-129, which includes deletion of a portion of the Akt1 hinge region) version of Akt1, PCR deletion mutagenesis was done using the full length Akt1 gene in the pS2neo vector as template. The PCR was carried out in 2 steps using overlapping internal primers (5' GAATACATGC-CGATGGAAAGCGACGGGGCTGAA-GAGATGGAGGTG 3' (SEQ.ID.NO.: 6), and 5' CCCCTC-CATCTCTTCAGCCCCGTCGCTTTCCATCGGCATG TATTC 3' (SEQ.ID.NO.: 7)) which encompassed the deletion and 5' and 3' flanking primers which encompassed the KpnI site and middle T tag on the 5' end. The final PCR product was digested with KpnI and SmaI and ligated into the pS2neo full length Akt1 KpnI/SmaI cut vector, effectively replacing the 5' end of the clone with the deleted version.

Human Akt3 gene was amplified by PCR of adult brain cDNA (Clontech) using the amino terminal oligo primer: 5' GAATTCAGATCTACCATGAGCGATGTTACCATTGTG 3' (SEQ.ID.NO.: 8); and the carboxy terminal oligo primer: 5' TCTAGATCTTATTCTCGTCCACTTGCAGAG 3' (SEQ.ID.NO.: 9). These primers included a 5' EcoRI/BglII site and a 3' XbaI/BglII site for cloning purposes. The resultant PCR product was cloned into the EcoRI and XbaI sites of pGEM4Z (Promega). For expression/purification purposes, a middle T tag was added to the 5' end of the full length Akt3 clone using the PCR primer: 5' GGTACCATGGAATACAT-GCCGATGGAAAGCGATGTTACCATTGTGAAG 3' (SEQ.ID.NO.: 10). The resultant PCR product encompassed a 5' KpnI site which allowed in frame cloning with the biotin tag containing insect cell expression vector, pS2neo.

Human Akt2 gene was amplified by PCR from human thymus cDNA (Clontech) using the amino terminal oligo primer: 5' AAGCTTAGATCTACCATGAATGAGGT-GTCTGTC 3' (SEQ.ID.NO.: 11); and the carboxy terminal oligo primer: 5' GAATTCGGATCCTCACTCGCGGAT-GCTGGC 3' (SEQ.ID.NO.: 12). These primers included a 5' HindIII/BglII site and a 3' EcoRI/BamHI site for cloning purposes. The resultant PCR product was subcloned into the HindIII/EcoRI sites of pGem3Z (Promega). For expression/purification purposes, a middle T tag was added to the 5' end of the full length Akt2 using the PCR primer: 5' GGTAC-CATGGAATACATGCCGATGGAAAATGAG-GTGTCTGTCATCAAAG 3' (SEQ.ID.NO.: 13). The resultant PCR product was subcloned into the pS2neo vector as described above.

Example 2

Expression of Human Akt Isoforms and ΔPH-Akt1

The DNA containing the cloned Akt1, Akt2, Akt3 and ΔPH-Akt1 genes in the pS2neo expression vector was purified and used to transfect *Drosophila* S2 cells (ATCC) by the calcium phosphate method. Pools of antibiotic (G418, 500 µg/ml) resistant cells were selected. Cell were expanded to a 1.0 L volume (~7.0×10$^6$ /ml), biotin and CuSO$_4$ were added to a final concentration of 50 µM and 50 mM respectively. Cells were grown for 72 h at 27° C. and harvested by centrifugation. The cell paste was frozen at −70° C. until needed.

Example 3

Purification of Human Akt Isoforms and ΔPH-Akt1

Cell paste from one liter of S2 cells, described in Example 13, was lysed by sonication with 50 mls 1% CHAPS in buffer A: (50 mM Tris pH 7.4, 1 mM EDTA, 1 mM EGTA, 0.2 mM AEBSF, 10 µg/ml benzamidine, 5 µg/ml of leupeptin, aprotinin and pepstatin each, 10% glycerol and 1 mM DTT). The soluble fraction was purified on a Protein G Sepharose fast flow (Pharmacia) column loaded with 9 mg/ml anti-middle T monoclonal antibody and eluted with 75 µM EYMPME (SEQ.ID.NO.: 14) peptide in buffer A containing 25% glycerol. Akt/PKB containing fractions were pooled and the protein purity evaluated by SDS-PAGE. The purified protein was quantitated using a standard Bradford protocol. Purified protein was flash frozen on liquid nitrogen and stored at −70° C.

Akt and Akt pleckstrin homology domain deletions purified from S2 cells required activation. Akt and Akt pleckstrin homology domain deletions was activated (Alessi et al. *Current Biology* 7:261-269) in a reaction containing 10 nM PDK1 (Upstate Biotechnology, Inc.), lipid vesicles (10 µM phosphatidylinositol-3,4,5-trisphosphate—Metreya, Inc, 100 µM phosphatidylcholine and 100 µM phosphatidylserine—Avanti Polar lipids, Inc.) and activation buffer (50 mM Tris pH7.4, 1.0 mM DTT, 0.1 mM EGTA, 1.0 µM Microcystin-LR, 0.1 mM ATP, 10 mM MgCl$_2$, 333 µg/ml BSA and 0.1 mM EDTA). The reaction was incubated at 22° C. for 4 hours. Aliquots were flash frozen in liquid nitrogen.

Example 4

Akt Kinase Assays

Activated Akt isoforms and pleckstrin homology domain deletion constructs were assayed utilizing a GSK-derived biotinylated peptide substrate. The extent of peptide phosphorylation was determined by Homogeneous Time Resolved Fluorescence (HTRF) using a lanthanide chelate (Lance)-coupled monoclonal antibody specific for the phosphopeptide in combination with a streptavidin-linked allophycocyanin (SA-APC) fluorophore which will bind to the biotin moiety on the peptide. When the Lance and APC are in proximity (i.e. bound to the same phosphopeptide molecule), a non-radiative energy transfer takes place from the Lance to the APC, followed by emission of light from APC at 665 nm.

Materials required for the assay:
A. Activated Akt isozyme or pleckstrin homology domain deleted construct B. Akt peptide substrate: GSK3α (S21) Peptide no.3928 biotin-GGRARTSSFAEPG (SEQ.ID.NO.:15), Macromolecular Resources.
C. Lance labeled anti-phospho GSK3α monoclonal antibody (Cell Signaling Technology, clone #27).
D. SA-APC (Prozyme catalog no. PJ25S lot no. 896067).
E. Microfluor®B U Bottom Microtiter Plates (Dynex Technologies, Catalog no. 7205).
F. Discovery® HTRF Microplate Analyzer, Packard Instrument Company.
G. 100×Protease Inhibitor Cocktail (PIC): 1 mg/ml benzamidine, 0.5 mg/ml pepstatin, 0.5 mg/ml leupeptin, 0.5 mg/ml aprotinin.
H. 10×Assay Buffer: 500 mM HEPES, pH 7.5, 1% PEG, mM EDTA, 1 mM EGTA, 1% BSA, 20 mM β-Glycerol phosphate.
I. Quench Buffer: 50 mM HEPES pH 7.3, 16.6 mM EDTA, 0.1% BSA, 0.1% Triton X-100, 0.17 nM Lance labeled monoclonal antibody clone #27, 0.0067 mg/ml SA-APC
J. ATP/MgCl$_2$ working solution: 1×Assay buffer, 1 mM DTT, 1×PIC, 125 mM KCl, 5% Glycerol, 25 mM MgCl$_2$, 375 μM ATP
K. Enzyme working solution: 1×Assay buffer, 1 mM DTT, 1×PIC, 5% Glycerol, active Akt. The final enzyme concentrations were selected so that the assay was in a linear response range.
L. Peptide working solution: 1×Assay buffer, 1 mM DTT, 1×PIC, 5% Glycerol, 2 μM GSK3 biotinylated peptide #3928

The reaction is assembled by adding 16 μL of the ATP/MgCl$_2$ working solution to the appropriate wells of a 96-well microtiter plate. Inhibitor or vehicle (1.0 μl) is added followed by 10 μl of peptide working solution. The reaction is started by adding 13 μl of the enzyme working solution and mixing. The reaction is allowed to proceed for 50 min and then stopped by the addition of 60 μl HTRF quench buffer. The stopped reactions were incubated at room temperature for at least 30 min and then read on the Discovery instrument.

PKA Assay:
Each individual PKA assay consists of the following components:
A. 5×PKA assay buffer (200 mM Tris pH7.5, 100 μM MgCl$_2$, 5 mM β-mercaptoethanol, 0.5 mM EDTA)
B. 50 μM stock of Kemptide (Sigma) diluted in water
C. $^{33}$P-ATP prepared by diluting 1.0 μl $^{33}$P-ATP [10 mCi/ml] into 200 μl of a 50 μM stock of unlabeled ATP
D. 10 μl of a 70 nM stock of PKA catalytic subunit (UBI catalog #14-114) diluted in 0.5 mg/ml BSA
E. PKA/Kemptide working solution: equal volumes of 5×PKA assay buffer, Kemptide solution and PKA catalytic subunit.

The reaction is assembled in a 96 deep-well assay plate. The inhibitor or vehicle (10 μl) is added to 10 μl of the $^{33}$P-ATP solution. The reaction is initiated by adding 30 μl of the PKA/Kemptide working solution to each well. The reactions were mixed and incubated at room temperature for 20 min. The reactions were stopped by adding 50 μl of 100 mM EDTA and 100 mM sodium pyrophosphate and mixing.

The enzyme reaction product (phosphorylated Kemptide) was collected on p81 phosphocellulose 96 well filter plates (Millipore). To prepare the plate, each well of a p81 filter plate was filled with 75 mM phosphoric acid. The wells were emptied through the filter by applying a vacuum to the bottom of the plate. Phosphoric acid (75 mM, 170 μl) was added to each well. A 30 μl aliquot from each stopped PKA reaction was added to corresponding wells on the filter plate containing the phosphoric acid. The peptide was trapped on the filter following the application of a vacuum and the filters were washed 5 times with 75 mM phosphoric acid. After the final wash, the filters were allowed to air dry. Scintillation fluid (30 μl) was added to each well and the filters counted on a Top-Count (Packard).

PKC Assay:
Each PKC assay consists of the following components:
A. 10×PKC co-activation buffer: 2.5 mM EGTA, 4 mM CaCl$_2$
B. 5×PKC activation buffer: 1.6 mg/ml phosphatidylserine, 0.16 mg/ml diacylglycerol, 100 mM Tris pH 7.5, 50 mM MgCl$_2$, 5 mM β-mercaptoethanol
C. $^{33}$P-ATP prepared by diluting 1.0 μl $^{33}$P-ATP [10 mCi/ml] into 100%1 of a 100 μl stock of unlabeled ATP
D. Myelin basic protein (350 μg/ml, UBI) diluted in water
E. PKC (50 ng/ml, UBI catalog #14-115) diluted into 0.5 mg/ml BSA
F. PKC/Myelin Basic Protein working solution: Prepared by mixing 5 volumes each of PKC co-activation buffer and Myelin Basic protein with 10 volumes each of PKC activation buffer and PKC.

The assays were assembled in 96 deep-well assay plates. Inhibitor or vehicle (10 μl) was added to 5.0 μl of $^{33}$P-ATP. Reactions were initiated with the addition of the PKC/Myelin Basic Protein working solution and mixing. Reactions were incubated at 30° C. for 20 min. The reactions were stopped by adding 50 μl of 100 mM EDTA and 100 mM sodium pyrophosphate and mixing. Phosphorylated Mylein Basic Protein was collected on PVDF membranes in 96 well filter plates and quantitated by scintillation counting.

Specific compounds of the instant invention were tested in the assay described above and were found to have IC$_{50}$ of ≦20 μM against one or more of Akt1, Akt2 and Akt3.

Example 5

Cell BASED ASSAYS to Determine Inhibition of Akt/PKB

Cells (for example LnCaP or a PTEN$^{(-/-)}$tumor cell line with activated Akt/PKB) were plated in 100 mM dishes. When the cells were approximately 70 to 80% confluent, the cells were refed with 5 mls of fresh media and the test compound added in solution. Controls included untreated cells, vehicle treated cells and cells treated with either LY294002 (Sigma) or wortmanin (Sigma) at 20 μM or 200 nM, respectively. The cells were incubated for 2, 4 or 6 hrs, and the media removed, The cells were washed with PBS, scraped and transferred to a centrifuge tube. They were pelleted and washed again with PBS. Finally, the cell pellet was resuspended in lysis buffer (20 mM Tris pH8, 140 mM NaCl, 2 mM EDTA, 1% Triton, 1 mM Na Pyrophosphate, 10 mM β-Glycerol Phosphate, 10 mM NaF, 0.5 mm NaVO$_4$, 1 μM Microsystine, and 1×Protease Inhibitor Cocktail), placed on ice for 15 minutes and gently vortexed to lyse the cells. The lysate was spun in a Beckman tabletop ultra centrifuge at 100,000×g at 4° C. for 20 min. The supernatant protein was quantitated by a standard Bradford protocol (BioRad) and stored at −70° C. until needed.

Proteins were immunoprecipitated (IP) from cleared lysates as follows: For Akt1/PKBα, lysates are mixed with Santa Cruz sc-7126 (D-17) in NETN (100 mM NaCl, 20 mM Tris pH 8.0, 1 mM EDTA, 0.5% NP-40) and Protein A/G Agarose (Santa Cruz sc-2003) was added. For Akt2/PKBβ, lysates were mixed in NETN with anti-Akt-2 agarose (Upstate Biotechnology #16-174) and for Akt3/PKBγ, lysates were mixed in NETN with anti-Akt3 agarose (Upstate Biotechnology #16-175). The IPs were incubated overnight at 4° C., washed and seperated by SDS-PAGE.

Western blots were used to analyze total Akt, pThr308 Akt1, pSer473 Akt1, and corresponding phosphorylation sites on Akt2 and Akt3, and downstream targets of Akt using specific antibodies (Cell Signaling Technology): Anti-Total Akt (cat. no. 9272), Anti-Phopho Akt Serine 473 (cat. no. 9271), and Anti-Phospho Akt Threonine 308 (cat. no. 9275). After incubating with the appropriate primary antibody diluted in PBS+0.5% non-fat dry milk (NFDM) at 4° C. overnight, blots were washed, incubated with Horseradish peroxidase (HRP)-tagged secondary antibody in PBS+0.5% NFDM for 1 hour at room temperature. Proteins were detected with ECL Reagents (Amersham/Pharmacia Biotech RPN2134).

Example 6

Heregulin Stimulated Akt Activation

MCF7 cells (a human breast cancer line that is PTEN$^{+/+}$) were plated at 1×10$^6$ cells per 100 mM plate. When the cells were 70-80% confluent, they were refed with 5 ml of serum free media and incubated overnight. The following morning, compound was added and the cells were incubated for 1-2 hrs, after which time heregulin was added (to induce the activation of Akt) for 30 minutes and the cells were analyzed as described above.

Example 7

Inhibition of Tumor Growth

In vivo efficacy of an inhibitor of the growth of cancer cells may be confirmed by several protocols well known in the art.

Human tumor cell lines which exhibit a deregulation of the PI3K pathway (such as LnCaP, PC3, C33a, OVCAR-3, MDA-MB-468 or the like) are injected subcutaneously into the left flank of 6-10 week old female nude mice (Harlan) on day 0. The mice are randomly assigned to a vehicle, compound or combination treatment group. Daily subcutaneous administration begins on day 1 and continues for the duration of the experiment. Alternatively, the inhibitor test compound may be administered by a continuous infusion pump. Compound, compound combination or vehicle is delivered in a total volume of 0.2 ml. Tumors are excised and weighed when all of the vehicle-treated animals exhibited lesions of 0.5-1.0 cm in diameter, typically 4 to 5.5 weeks after the cells were injected. The average weight of the tumors in each treatment group for each cell line is calculated.

What is claimed is:

1. A compound of the formula A:

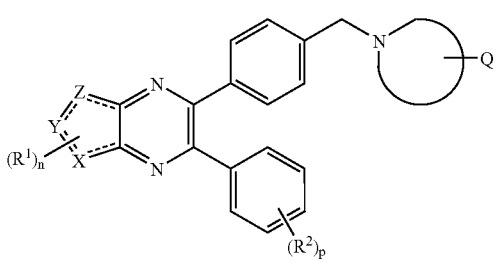

wherein:
n is 0, 1, 2 or 3;
p is 0, 1, 2 or 3;
r is 0 or 1;
s is 0 or 1;
m is 0 or 1;
a is 0 or 1;
b is 0 or 1;
X, Y and Z are independently selected from: C, N, S or O provided that at least one of X, Y or Z is N, S or O;

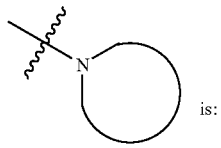

is:

heterocycle, optionally substituted with one to three $R^z$;
Q is selected from: H, —$NR^5R^6$ and heterocycle, said heterocycle which is optionally substituted with one to three $R^z$;
$R^1$ and $R^2$ are independently selected from:
1) $(C=O)_aO_bC_1-C_{10}$ alkyl,
2) $(C=O)_aO_b$ aryl,
3) $C_2-C_{10}$ alkynyl,
4) $C_2-C_{10}$ alkynyl,
5) $(C=O)_aO_b$ heterocyclyl,
6) $(C=O)_aO_bC_3-C_8$ cycloalkyl,
7) $CO_2H$,
8) halo,
9) CN,
10) OH,
11) $O_bC_1-C_6$ perfluoroalkyl,
12) $O_a(C=O)_bNR^3R^4$,
13) $NR^c(C=O)NR^3R^4$,
14) $S(O)_mR^a$,
15) $S(O)_2NR^3R^4$,
16) $NR^cS(O)_mR^a$,
17) oxo,
18) CHO,
19) $NO_2$,
20) $NR^c(C=O)O_bR^a$,
21) $O(C=O)O_bC^1-C^{10}$ alkyl,
22) $O(C=O)O_bC_3-C_8$ cycloalkyl,
23) $O(C=O)O_b$ aryl, and
24) $O(C=O)O_b$-heterocycle,
said alkyl, aryl, alkenyl, alkynyl, heterocyclyl, and cycloalkyl optionally with one or more substituents selected from $R^z$;

$R^3$ and $R^4$ are independently selected from:
1) H,
2) $(C=O)_aO_bC_1-C_{10}$ alkyl,
3) $(C=O)_aO_b$ aryl,
4) $C_2-C_{10}$ alkenyl,
5) $C_2-C_{10}$ alkynyl,
6) $(C=O)_aO_b$ heterocyclyl,
7) $(C=O)_aO_bC_3-C_8$ cycloalkyl,
8) OH,
9) $C_1-C_6$ perfluoroalkyl,
10) $S(O)_mR^a$, and
11) CHO,
said alkyl, cycloalkyl, aryl, heterocylyl, alkenyl, and alkynyl is optionally substituted with one or more substituents selected from $R^z$, or
$R^3$ and $R^4$ can be taken together with the nitrogen to which they are attached to form a monocyclic or bicyclic heterocycle with 4-7 members in each ring and optionally containing, in addition to the nitrogen, 1-3 heteroatoms selected from N, O and S, said monocyclic or bicyclic heterocycle optionally substituted with one or more substituents selected from $R^z$;

$R^5$ and $R^6$ are independently selected from:
1) H,
2) $(C=O)_aO_bC_1-C_{10}$ alkyl,
3) $(C=O)_aO_b$ aryl,
4) $C_2-C_{10}$ alkenyl,
5) $C_2-C_{10}$ alkynyl,
6) $(C=O)_aO_b$ heterocyclyl,
7) $(C=O)_aO_bC_3-C_8$ cycloalkyl,
8) OH,
9) $C_1-C_6$ perfluoroalkyl,
10) $(C=O)NR^3R^4$,
11) $S(O)_mR^a$,
12) $S(O)_2NR^3R^4$, and
13) CHO,
said alkyl, cycloalkyl, aryl, heterocylyl, alkenyl, and alkynyl is optionally substituted with one or more substituents selected from $R^z$, or
$R^5$ and $R^6$ can be taken together with the nitrogen to which they are attached to form a monocyclic or bicyclic heterocycle with 4-7 members in each ring and optionally containing, in addition to the nitrogen, 1-3 heteroatoms selected from N, O and S, said monocyclic or bicyclic heterocycle optionally substituted with one or more substituents selected from $R^z$;

$R^z$ is selected from:
1) $(C=O)_rO_s(C_1-C_{10})$alkyl,
2) $O_r(C_1-C_3)$perfluoroalkyl,
3) $(C_0-C_6)$alkylene-$S(O)_mR^a$,
4) oxo,
5) OH,
6) halo,
7) CN,
8) $(C=O)_rO_s(C_2-C_{10})$alkenyl,
9) $(C=O)_rO_s(C_2-C_{10})$alkynyl,
10) $(C=O)_rO_s(C_3-C_6)$cycloalkyl,
11) $(C=O)_rO_s(C_0-C_6)$alkylene-aryl,
12) $(C=O)_rO_s(C_0-C_6)$alkylene-heterocyclyl,
13) $(C=O)_rO_s(C_0-C_6)$alkylene-$N(R^b)_2$,
14) $C(O)R^a$,
15) $(C_0-C_6)$alkylene-$CO_2R^a$,
16) $C(O)H$,
17) $(C_0-C_6)$alkylene-$CO_2H$,
18) $C(O)N(R^b)_2$,
19) $S(O)_mR^a$,
20) $NR^c(C=O)O_bR^a$, 21) $O(C=O)O_bC_1-C_{10}$ alkyl,
22) $O(C=O)O_bC_3-C_8$ cycloalkyl,
23) $O(C=O)O_b$ aryl, and
24) $O(C=O)O_b$-heterocycle, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;

$R^a$ is substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_6)$cycloalkyl, substituted or unsubstituted aryl, $(C_1-C_6)$perfluoroalkyl, 2,2,2-trifluoroethyl, or substituted or unsubstituted heterocyclyl; and $R^b$ is H, $(C_1-C_6)$alkyl, substituted or unsubstituted aryl, substituted or unsubstituted benzyl, substituted or unsubstituted heterocyclyl, $(C_3-C_6)$cycloalkyl, $(C=O)OC_1-C_6$ alkyl, $(C=O)C_1-C_6$ alkyl or $S(O)_2R^a$;

$R^c$ is selected from:
1) H,
2) $C_1-C_{10}$ alkyl,
3) aryl,
4) $C_2-C_{10}$ alkenyl,
5) $C_2-C_{10}$ alkynyl,
6) heterocyclyl,
7) $C_3-C_8$ cycloalkyl,
8) $C_1-C_6$ perfluoroalkyl, said alkyl, cycloalkyl, aryl, heterocylyl, alkenyl, and alkynyl is optionally substituted with one or more substituents selected from $R^z$;

or a pharmaceutically acceptable salt or a stereoisomer thereof.

2. The compound according to claim 1 wherein:
n is 0 or 1;

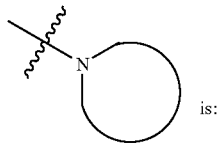
is:

heterocycle selected from 2-azepinone, benzimidazolyl, benzimidazolonyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl, said heterocycle optionally substituted with one to three $R^z$;

Q is selected from: H and $-NR^5R^6$;

$R^1$ and $R^2$ are independently selected from:
1) $(C=O)_aO_bC_1-C_{10}$ alkyl,
2) $(C=O)_aO_b$ aryl,
3) $C_2-C_{10}$ alkenyl,
4) $C_2-C_{10}$ alkynyl,
5) $(C=O)_aO_b$ heterocyclyl,
6) $(C=O)_aO_bC_3-C_8$ cycloalkyl,
7) $CO_2H$,
8) halo,
9) CN,
10) OH,
1) $O_bC_1-C_6$ perfluoroalkyl,
2) $S(O)_mR^a$,
3) $NR^cS(O)_mR^a$,
4) oxo,
5) CHO,
6) $NO_2$,
7) $NR^c(C=O)O_bR^a$,
8) $O(C=O)O_bC_1-C_{10}$ alkyl,
9) $O(C=O)O_bC_3-C_8$ cycloalkyl,
10) $O(C=O)O_b$ aryl,
11) $O(C=O)O_b$-heterocycle, and
12) $NH_2$, said alkyl, aryl, alkenyl, alkynyl, heterocyclyl, and cycloalkyl optionally substituted with one or more substituents selected from $R^z$;

or a pharmaceutically acceptable salt or a stereoisomer thereof.

3. The compound according to claim 2 wherein:

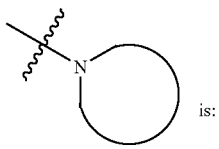
is:

heterocycle selected from

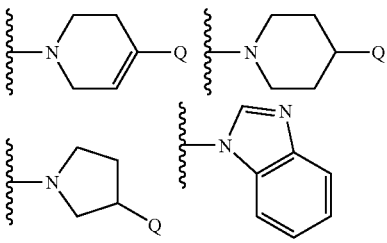

said heterocycle optionally substituted with one to three $R^z$;

Q is selected from: $-NR^5R^6$;

$R^5$ and $R^6$ are independently selected from:
1) H,
2) $(C=O)_aO_bC_1-C_{10}$ alkyl,
3) $(C=O)_aO_b$ aryl,
4) $C_2-C_{10}$ alkenyl,
5) $C_2-C_{10}$ alkynyl,
6) $(C=O)_aO_b$ heterocyclyl,
7) $(C=O)_aO_bC_3-C_8$ cycloalkyl,
8) OH,
9) $C_1-C_6$ perfluoroalkyl,
10) $S(O)_mR^a$, and
11) CHO, said alkyl, cycloalkyl, aryl, heterocylyl, alkenyl, and alkynyl is optionally substituted with one or more substituents selected from $R^z$, or $R^5$ and $R^6$ can be taken together with the nitrogen to which they are attached to form a monocyclic or bicyclic heterocycle with 4-7 members in each ring and optionally containing, in addition to the nitrogen, 1-3 heteroatoms selected from N, O and S, said monocyclic or bicyclic heterocycle optionally substituted with one or more substituents selected from $R^z$;

or a pharmaceutically acceptable salt or a stereoisomer thereof.

4. The compound according to claim 3 wherein:
Q is selected from:

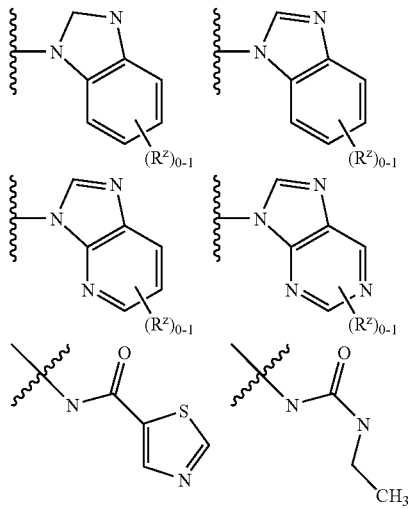

wherein $R^z$ can attach anywhere on the bicyclic structure;
$R^1$ and $R^2$ are independently selected from:
1) $(C_1-C_6)$alkyl,
2) $(C_1-C_{10})$alkyl-OH
3) $CO_2H$,
4) halo,
5) CN,
6) OH,
7) oxo,
8) CHO,
9) $NO_2$, and
10) $NH_2$ $R^z$ is independently selected from:
1) $(C_1-C_6)$alkyl,
2) $(C_1-C_{10})$alkyl-OH
3) $CO_2H$,
4) halo,
5) CN,
6) OH,
7) oxo,
8) CHO,
9) $NO_2$, and
10) $NH_2$ or a pharmaceutically acceptable salt or a stereoisomer thereof.

5. A compound which is selected from:
1-{1-[4-(3-phenylthieno[3,4-b]pyrazin-2-yl)benzyl]piperidin-4-yl}-1,3-dihydro-2H-benzimidazol-2-one;
N-ethyl-N'-{(3R)-1-[4-(3-phenylthieno[3,4-b]pyrazin-2-yl)benzyl]pyrrolidin-3-yl}urea;
N-{(3R)-1-[4-(3-phenylthieno[3,4-b]pyrazin-2-yl)benzyl]pyrrolidin-3-yl}-1,3-thiazole-5-carboxamide;
9-{1-[4-(3-phenylthieno[3,4-b]pyrazin-2-yl)benzyl]piperidin-4-yl}-9H-purin-6-amine;
2-(4-{[4-(3H-imidazo[4,5-b]pyridin-3-yl)piperidin-1-yl]methyl}phenyl)-3-phenylthieno[3,4-b]pyrazine;
9-{(1-[4-(3-phenylthieno[3,4-b]pyrazin-2-yl)benzyl]piperidin-4-yl}-9H-purine;
{1-[4-(3-phenylthieno[3,4-b]pyrazin-2-yl)benzyl]-1H-benzimidazol-2-yl}methanol;
2-{4-[(2-methyl-1H-benzimidazol-1-yl)methyl]phenyl}-3-phenylthieno[3,4-b]pyrazine;
1-{1-[4-(3-phenylthieno[3,4-b]pyrazin-2-yl)benzyl]-1,2,3,6-tetrahydropyridin-4-yl}-1,3-dihydro-2H-benzimidazol-2-one;
N-{(3R)-1-[4-(3-hydroxy-5-phenyl-2H-pyrazolo[3,4-b]pyrazin-6-yl)benzyl]pyrrolidin-3-yl}-1,3-thiazole-5-carboxamide; and
1-{1-[4-(3-hydroxy-5-phenyl-2H-pyrazolo[3,4-b]pyrazin-6-yl)benzyl]piperidin-4-yl}-1,3-dihydro-2H-benzimidazol-2-one;
or a pharmaceutically acceptable salt or a stereoisomer thereof.

6. The TFA salt of a compound according to claim 1 which is:
1-{1-[4-(3-phenylthieno[3,4-b]pyrazin-2-yl)benzyl]piperidin-4-yl}-1,3-dihydro-2H-benzimidazol-2-one;
N-ethyl-N'-{(3R)-1-[4-(3-phenylthieno[3,4-b]pyrazin-2-yl)benzyl]pyrrolidin-3-yl}urea;
N-{(3R)-1-[4-(3-phenylthieno[3,4-b]pyrazin-2-yl)benzyl]pyrrolidin-3-yl}-1,3-thiazole-5-carboxamide;
9-{1-[4-(3-phenylthieno[3,4-b]pyrazin-2-yl)benzyl]piperidin-4-yl}-9H-purin-6-amine;
2-(4-{[4-(3H-imidazo[4,5-b]pyridin-3-yl)piperidin-1-yl]methyl}phenyl)-3-phenylthieno[3,4-b]pyrazine;
9-{1-[4-(3-phenylthieno[3,4-b]pyrazin-2-yl)benzyl]piperidin-4-yl}-9H-purine;
{1-[4-(3-phenylthieno[3,4-b]pyrazin-2-yl)benzyl]-1H-benzimidazol-2-yl}methanol;
2-{4-[(2-methyl-1H-benzimidazol-1-yl)methyl]phenyl}-3-phenylthieno[3,4-b]pyrazine;
1-{1-[4-(3-phenylthieno[3,4-b]pyrazin-2-yl)benzyl]-1,2,3,6-tetrahydropyridin-4-yl }-1,3-dihydro2H-benzimidazol-2-one;
N-{(3R)-1-[4-(3-hydroxy-5-phenyl-2H-pyrazolo[3,4-b]pyrazin-6-yl)benzyl]pyrrolidin-3-yl}-1,3-thiazole-5-carboxamide; and
1-{1-[4-(3-hydroxy-5-phenyl-2H-pyrazolo[3,4-b]pyrazin-6-yl)benzyl]piperidin-4-yl}-1,3-dihydro-2H-benzimidazol-2-one;
or a stereoisomer thereof.

7. A compound according to claim 5 which is selected from:
1-{1-[4-(3-phenylthieno[3,4-b]pyrazin-2-yl)benzyl]piperidin-4-yl}-1,3-dihydro-2H-benzimidazol-2-one;
or a pharmaceutically acceptable salt or a stereoisomer thereof.

8. A pharmaceutical composition comprising a pharmaceutical carrier, and dispersed therein, a therapeutically effective amount of a compound of claim 1.

9. A pharmaceutical composition comprising a pharmaceutical carrier, and dispersed therein, a therapeutically effective amount of a compound of claim 6.

\* \* \* \* \*